United States Patent
Repka et al.

(10) Patent No.: US 10,335,381 B2
(45) Date of Patent: *Jul. 2, 2019

(54) STABILIZED FORMULATION OF TRIAMCINOLONE ACETONIDE

(71) Applicant: University of Mississippi, Oxford, MS (US)

(72) Inventors: Michael A Repka, Oxford, MS (US); Angela Sutterer, St. Louis, MO (US)

(73) Assignee: University of Mississippi, University, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/783,208

(22) Filed: Oct. 13, 2017

(65) Prior Publication Data

US 2018/0036263 A1 Feb. 8, 2018

Related U.S. Application Data

(63) Continuation of application No. 12/299,753, filed as application No. PCT/US2007/068496 on May 8, 2007, now Pat. No. 9,801,837.

(60) Provisional application No. 60/798,483, filed on May 8, 2006.

(51) Int. Cl.
| | |
|---|---|
| *A61K 31/167* | (2006.01) |
| *A61K 31/194* | (2006.01) |
| *A61K 31/573* | (2006.01) |
| *A61K 9/00* | (2006.01) |
| *A61K 47/10* | (2017.01) |
| *A61K 47/14* | (2017.01) |
| *A61K 47/32* | (2006.01) |

(52) U.S. Cl.
CPC ............ *A61K 31/167* (2013.01); *A61K 9/006* (2013.01); *A61K 31/194* (2013.01); *A61K 31/573* (2013.01); *A61K 47/10* (2013.01); *A61K 47/14* (2013.01); *A61K 47/32* (2013.01)

(58) Field of Classification Search
CPC .. A61K 31/167; A61K 31/194; A61K 31/573; A61K 9/006; A61K 47/10; A61K 47/14; A61K 47/32
See application file for complete search history.

(56) References Cited

U.S. PATENT DOCUMENTS

| | | | |
|---|---|---|---|
| 4,615,697 A | 10/1986 | Robinson | |
| 4,772,470 A * | 9/1988 | Inoue | A61K 9/006 424/435 |
| RE33,093 E | 10/1989 | Schiradli et al. | |
| 4,910,247 A | 3/1990 | Haldar et al. | |
| 4,948,580 A | 8/1990 | Browning | |
| 5,112,620 A | 5/1992 | Repka et al. | |
| 5,714,165 A | 2/1998 | Repka | |
| 5,928,213 A | 7/1999 | Barney | |
| 6,375,963 B1 | 4/2002 | Repka | |
| 2006/0076536 A1 | 4/2006 | Barshied | |

OTHER PUBLICATIONS

Gupta, V.D., Stability of Triamcinolone Acetonide Solutions as Determined by High-Performance Liquid Chromatography, J. Pharm. Sci. 72(12),1453-1456 (1983).
Ungphaiboon et al., Formulation and efficacy of triamcinolone acetonide mouthwash for treating oral lichen planus, Am J. Health-Syst. Pharm., 62:485-491 (2005).
Xu et al., Simultaneous determination of lignocaine hydrochloride, chlorhexidine gluconate, and triamcinolone acetonide in suspension by reversed—phase HPLC, J. Liq. Chrom & Re. Technol., 22(13): 2071-2091 (1999).
Templeton, et al.; Rapid Headspace Oxygen Analysis for Pharmaceutical Packaging Applications; Pharmaceutical Tech; Jul. 1, 2002; pp. 44-61.

* cited by examiner

*Primary Examiner* — Sarah Pihonak
(74) *Attorney, Agent, or Firm* — Stites & Harbison PLLC; Richard S. Myers, Jr.

(57) ABSTRACT

A stabilized formulation of triamcinolone acetonide in a bioadhesive base material is provided. The present invention further includes a method of producing a stabilized non-aqueous TAA formulation and methods of measuring the stability of such TAA formulations.

10 Claims, 13 Drawing Sheets

STABILIZED FORMULATION OF TRIAMCINOLONE ACETONIDE

CROSS REFERENCE TO RELATED APPLICATIONS

This application is a continuation of U.S. Pat. No. 9,801,837, filed Nov. 5, 2008, which claims priority to PCT/US07/68496, filed May 8, 2007, which claims benefit of U.S. Application No. 60/798,483, filed May 8, 2006.

FIELD OF THE INVENTION

The present invention is generally related to a storage stable triamcinolone acetonide (TAA) formulation. In particular, the present invention relates to bioadhesive formulations containing TAA and lidocaine or salt thereof, which are stable under standard storage conditions. In particular, the present invention relates to a process for the preparation of storage stable bioadhesive formulations containing TAA.

BACKGROUND OF THE INVENTION

Recurrent aphthous ulcers (RAU) or oral canker sores are the most common oral lesions afflicting humans. Studies have shown such ulcers affect 18% to 50% of the general population. As the name suggests, RAU lesions tend to recur in susceptible patients, often lasting for weeks. These lesions can be characterized as necrotizing ulcerations of oral mucosal tissue which are located on soft, non-keratinized mucosa. The lesions are painful, affect nutritional intake, and disrupt oral hygiene. They lead commonly to secondary infections by opportunistic organisms and sometimes result in scarring.

The etiology of RAU has been linked to several causative factors including allergies, trauma, stress, autoimmune dysfunction, nutritional deficiencies, microbial infection, hormonal changes, and systemic disease. However, several studies have shown that whatever the specific etiology in a particular patient, the clinical manifestations of RAU are due to an altered immune response. Immunosuppressive steroids such as triamcinolone acetonide are known to be effective in the treatment of RAU. A problem with steroidal therapy for RAU however, is that administration in large doses or over extended periods can cause adrenal suppression and atrophy. The dosage necessary for steroidal therapy to have therapeutic effect for RAU can be lessened, thereby decreasing the opportunity and magnitude of harmful side effects, if the therapy is applied topically rather than systemically. Furthermore, treatment periods necessary to achieve the desired therapeutic effect can be shortened if the form of the product encourages patient compliance in applying the medication on a prescribed schedule.

Attempts at delivery of medication to the oral mucosa have included bioadhesive compositions based primarily on organic cellulose, such as disclosed in Reissue Pat. No. RE 33,093 issued to Schiraldi et al., and polycarbophils disclosed in U.S. Pat. No. 4,615,697 issued to Robinson. The major disadvantages of such compositions is that they are aqueous systems which do not provide as rapid symptomatic relief as the compositions of the present invention, and which are relatively easily removed from the oral mucosa by the flow of saliva.

U.S. Pat. No. 4,948,580 to Browning describes a bioadhesive composition comprising a freeze-dried polymer mixture formed of the copolymer poly(methyl vinyl ether/maleic anhydride) and gelatin dispersed in an ointment base such as mineral oil containing dispersed polyethylene. The freeze-dried combination of polymer and gelatin is reported to be a synergistic combination having enhanced mucoadhesive properties compared to a simple mixture.

U.S. Pat. Nos. 5,112,620 and 5,714,165 to Repka describe combining the therapeutic effect of steroids to counter the dysfunctional immune response associated with RAU, with a local anesthetic to provide immediate symptomatic relief, in an organic base material which provides delivery of the active medications to the lesions. The base material is a bioadhesive composition having wet adherent properties which is not readily displaced from the oral mucosa even in the presence of saliva, and which allows the active medications to remain concentrated and localized over the RAU lesions for an extended treatment period. A formulation prepared in accordance with the Repka patents, containing 0.1% TAA and 2% lidocaine, was able to maintain at least 90% of the initial TAA concentration for 3 months under accelerated storage conditions of 40° C. and 75% relative humidity; however, surprisingly, the formulation was unable to maintain at least 90% of its initial concentration of TAA for more than 13 months under standard storage conditions of 25° C. and 60% relative humidity.

Ideally, a therapeutic composition has an extended shelf life. Due to the realities of production, distribution, and retail sales, product preferably has a shelf life of at least 12 months, preferably at least 18 months, more preferably at least 24 months, and still more preferably at least 36 months. Such a characteristic is particularly advantageous in the treatment of RAU because the ulcers reoccur in susceptible patients. A TAA formulation with a long shelf life would speed healing by allowing susceptible patients to keep the therapeutic formulation on hand so they may apply the formulation at the first appearance of the ulcer(s).

The U.S. Food and Drug Administration measures shelf life as the time (days/months) for which a product retains, within specified limits, the same properties and characteristics that it possessed at the time of its manufacture. [Reference—Guideline for Industry—Stability Testing of New Drug Substances and Products, ICH]. The "specified limits" for Formulation B of Example 1 are: TAA concentration of 90-110% w/w and lidocaine concentration of 95-105% w/w of label claim.

Methods of stabilizing aqueous and alcoholic solutions of TAA are known. TAA has been stabilized in aqueous solutions with an acidic pH. Gupta reports that the optimum pH for TAA stability in aqueous solution was measured to be about 3.4 (Gupta, V. D., "Stability of triamcinolone acetonide solutions as determined by high-performance liquid chromatography," *J. Pharm. Sci.*, 72:1453-6 (1983)). Ungphaiboon et al. report that decomposition of TAA in aqueous solutions was minimal at pH 3.4 and that above pH 5.5 the rate of TAA decomposition increased rapidly (Ungphaiboon et al., "Formulation and efficacy of triamcinolone acetonide mouthwash for treating oral lichen planus," *Am. J. Health-Syst. Pharm.*, 62:485-91 (2005)). Ungphaiboon et al. suggest that buffering agents and antioxidants may be added to a TAA formulation to increase its stability. Xu et al. reported that solutions containing lidocaine hydrochloride, chlorhexidine gluconate, and TAA were stable with respect to TAA degradation after storage at room temperature for one year. (Xu et al., "Simultaneous determination of lignocaine hydrochloride, chlorhexidine gluconate, and triamcinolone acetonide in suspension by reversed-phase HPLC," *J. Liq. Chrom. & Re. Technol.*, 22(13):2071-91 (1999)).

The Repka patents suggest stabilizing a bioadhesive TAA formulation by the addition of antioxidants such as butylated hydroxytoluene and butylated hydroxyanisole. However, it has been discovered that these antioxidants were not effective in adequately prolonging the storage stability of the Repka based formulation. Accordingly, there is a need for such compositions having enhanced storage stability.

SUMMARY OF THE INVENTION

Among the several features of the present invention are bioadhesive formulations with increased TAA stability and a process for producing such stable formulations.

Briefly, the present invention is directed to a storage stable therapeutic composition having wet adherent properties comprising a base material, about 0.01 to about 0.3 wt. % triamcinolone acetonide, and about 0.25 to about 6 wt. % lidocaine or a salt thereof. The base material comprises from about 3 to 15 wt. % of a water soluble salt of a copolymer of a lower alkyl vinyl ether and maleic acid or anhydride and from about 85 to 97 wt. % of a polyalkylene glycol. The composition comprises either: at least 90% of the triamcinolone acetonide based on the amount of the triamcinolone acetonide within the composition at the time of manufacture after 14 months storage at 25° C. and 60% relative humidity; no more than about 10% of compounds having the formulae I, II, and III based upon the amount of the triamcinolone acetonide within the composition at the time of manufacture after 14 months storage at 25° C. and 60% relative humidity; at least 90% of the triamcinolone acetonide based upon the amount of the triamcinolone acetonide within the composition at the time of manufacture after 6 months accelerated stability storage at 40° C. and 75% relative humidity; or no more than about 10% of the compounds having the formulae I, II, and III based upon the amount of said triamcinolone acetonide within the composition at the time of manufacture after 6 months accelerated stability storage at 40° C. and 75% relative humidity. In an embodiment, a composition having wet adherent properties comprises a base material, about 0.1 wt. % triamcinolone acetonide, and about 2 wt. % lidocaine or a salt thereof, which comprises at least 0.09 wt. % triamcinolone acetonide and 1.8 wt. % lidocaine or a salt thereof after 14 months; or comprises no more than about 0.01 wt. % of compounds having the formulae I, II, and III after 14 months.

Another aspect of the invention is directed to a composition for the treatment of mouth sores comprising a polyalkylene glycol, a water soluble salt of a copolymer of a lower alkyl vinyl ether and maleic acid or anhydride, lidocaine hydrochloride, triamcinolone acetonide, and a preservative.

In another aspect, the invention is directed to a method of making a therapeutic composition. The process comprises providing a base material and mixing lidocaine or a salt thereof and triamcinolone acetonide with the base material in an inert atmosphere.

DETAILED DESCRIPTION

Figure 1:
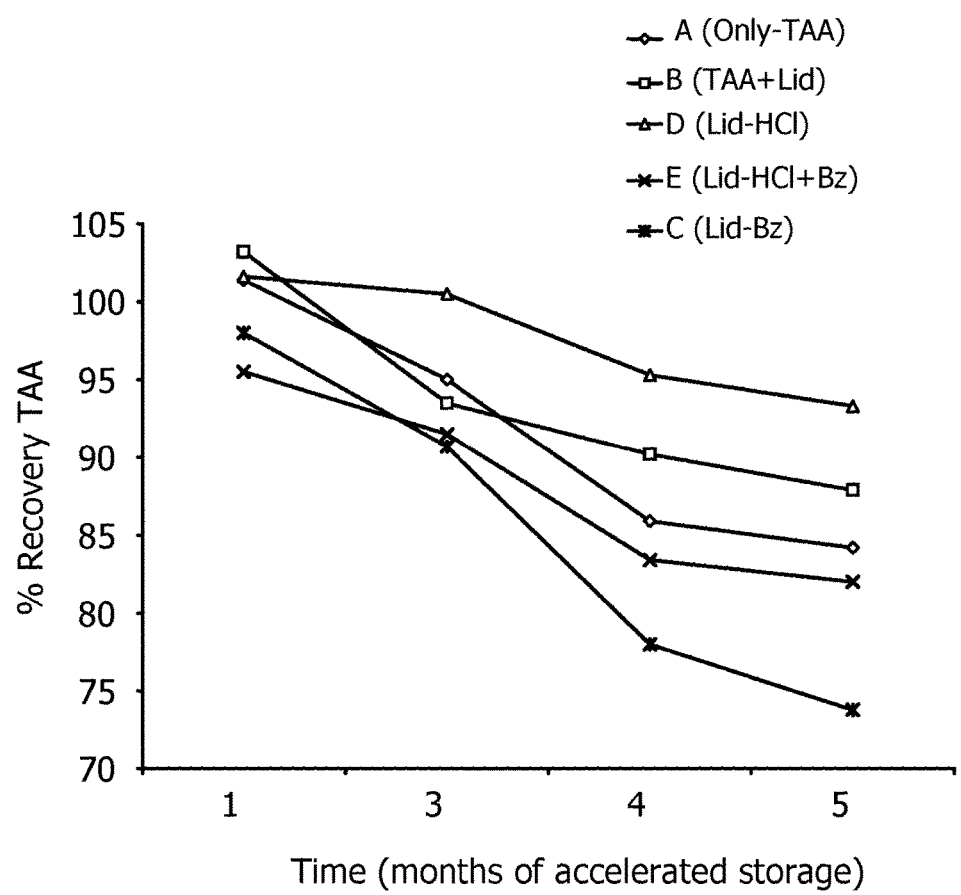
FIG. 1 is a graph depicting the stability of various TAA and lidocaine formulations as a percent recovery of TAA versus time as described in greater detail in the examples. "macc" is months of accelerated storage.

In accordance with the present invention, improved formulations with increased stability of TAA have been discovered. The present invention improves the shelf life of TAA and lidocaine or lidocaine salt bioadhesive formulations. It has been discovered that the shelf life of a TAA-containing formulation is significantly increased by selecting a lidocaine salt, such as lidocaine hydrochloride, rather than lidocaine free base for incorporation in the formulation because TAA degradation is reduced. While not being bound by any particular theory, it is believed that lidocaine hydrochloride is a more effective stabilizing agent within the formulation than is lidocaine free base. The present invention also includes a method of preparing the improved formulations in an inert atmosphere to minimize oxidative degradation of the formulations during storage. TAA-containing formulations including lidocaine or a salt thereof exhibit increased storage stability when prepared in an inert atmosphere as compared to formulations prepared under conventional conditions.

The formulations of the present invention comprise a base material and active ingredients.

Base Material

The therapeutic compositions of the present invention comprise a base material having wet adherent properties and a therapeutically effective amount of one or more medicaments incorporated in the base material. The base material is a bioadhesive composition comprising a polyalkylene glycol, and in particular polyethylene glycol (PEG), and from about 3 to 15 wt. % of a water-soluble salt of a copolymer of a lower alkyl vinyl ether and maleic acid or maleic anhydride. The PEG preferably comprises a mixture of a low molecular weight PEG which is a liquid at 30° C. and a high molecular weight PEG which is a waxy solid at 30° C. in proportions which result in the mixture having an ointment like consistency at room temperature. Suitable mixtures comprise from about 40 to about 60 wt. % PEG having a molecular weight of less than 600, most preferably PEG 400, admixed with about 20 to about 50 wt. % PEG having a molecular weight above 600, most preferably PEG 3350. The PEG component of the bioadhesive composition may conform to that described for ointments in the official monograph of the U.S. Pharmacopoeia (1990) at page 1963.

The alkyl vinyl ether/maleic acid or anhydride copolymers suitable for use in the base material are described in U.S. Pat. No. 4,910,247, incorporated herein by reference. In general, these copolymers have from about 40 to about 90%, preferably from about 70 to 90%, of the initial carboxyl groups reacted with a metal, and have a molecular weight of between about 18,000 and about 80,000, preferably between about 40,000 and about 60,000 as measured by membrane osmometry in 2-butanone (1-10 grams/1000 ml solution). The various metal salts of the copolymer can be prepared by reacting the desired amount of metal hydroxide with a lower alkyl vinyl ether/maleic acid or maleic anhydride copolymer having a molecular weight of from about 18,000 to about 80,000. Such alkyl vinyl ether/maleic acid or anhydride copolymers are commercially available from ISP Corporation and sold as GANTREZ™ S series (MW approximately equal to 18,000-70,000; MS series (MW approximately equal to 60,000-75,000) and AN series (MW approximately equal to 18,000-80,000). The resultant metal salt product in which a portion of the original carboxyl groups are neutralized, is then dried and milled to a suitable particle size.

For purposes of the present invention, the copolymer is preferably a blend comprising a divalent calcium salt and a monovalent sodium salt of a methyl vinyl ether/maleic acid copolymer wherein the concentration of Ca is between about 10 and 15 wt. % of the blend; the concentration of Na is between about 1.5 and about 4 wt. % of the blend, and free acid-COOH represents between about 9 and about 25 wt. % of the blend. Alternatively, a commercially available mixed calcium and sodium salt of a methyl vinyl ether/maleic acid or anhydride copolymer can be used in the present mixture. Such a polymeric salt blend is supplied by ISP Corporation as GANTREZ™ MS-955 (CAS #62386-95-2) wherein the concentration of Ca is between about 11 and 13 wt. % of the blend, the concentration of Na is between about 2 and 2.5 wt. % of the blend, the proportion of Ca:Na is about 5-6:1 and the molecular weight is about 65,000-70,000.

Active Ingredients

The medicament incorporated in the therapeutic compositions of the present invention may be any therapeutically active agent or combination of agents useful in the topical treatment of wounds, rashes, ulcers, and other conditions. For the treatment of aphthous ulcers, the medicament is preferably the immunosuppressive steroid TAA.

In addition, the therapeutic composition also includes a topical anesthetic such as lidocaine, benzocaine, bupivacaine, cocaine, dyclonine, mepivacaine, procaine, prilocaine, propoxycaine, chloroprocaine, tetracaine or salts thereof. Preferably, the anesthetic is lidocaine or a salt thereof, more preferably the anesthetic is lidocaine hydrochloride.

As will be described in Example 1 below, the addition of lidocaine to the formulation has a stabilizing effect on TAA in the base material. This stability effect can be seen by comparing Tables 1 and 2. Lidocaine hydrochloride had a marked effect on the stability of TAA in the formulation. In Example 2, a parallel five-month accelerated stability investigation revealed that the use of lidocaine hydrochloride increased the stability of the TAA formulation approximately 50%. The lidocaine hydrochloride was found to be a better stabilizer than lidocaine in the free base form. This result was particularly surprising because it was counterintuitive to add the salt of an active ingredient to a non-aqueous mixture rather than adding free base.

In addition to the active medicaments and anesthetic, the therapeutic compositions of the present invention can contain other components to modify the physical or esthetic properties thereof, such as coloring agents, flavoring agents, viscosity modifiers, gelling agents, antioxidants, preservatives and the like. Conventional preservatives such as methylparaben and propylparaben, and mixtures thereof and antioxidants such as butylated hydroxytoluene (BHT) and butylated hydroxyanisole (BHA) may also be included to prevent bacterial contamination. However, it has been found through experimentation that the addition of butylated hydroxytoluene or butylated hydroxyanisole did not increase the stability of TAA in the formulations described in the Repka patents. Therefore, these additives need not be added to increase stability, but can be added to facilitate another characteristic of the formulation such as antibacterial properties. Moreover, these additives need not be present in the therapeutic compositions at all. Therefore, particular embodiments of the therapeutic compositions may be free of additives such as, for example, butylated hydroxytoluene, butylated hydroxyanisole, and EDTA. Accordingly, in one embodiment, the compositions are free of butylated hydroxytoluene, butylated hydroxyanisole, or both. In another embodiment, the compositions are free of EDTA. In another embodiment, the present compositions are free of butylated hydroxytoluene, butylated hydroxyanisole, EDTA, or any combination thereof. In a particularly preferred embodiment, the compositions are free of butylated hydroxytoluene, butylated hydroxyanisole, and EDTA.

In addition, the therapeutic compositions may also contain antioxidants, and in particular, antioxidants that act as reducing agents or oxygen scavengers. Without being bound by any particular theory, it is believed that the instability of TAA is at least in part due to the presence of oxygen in the prior formulated TAA containing compounds. Accordingly, the use of antioxidants capable of scavenging oxygen, and in particular oxygen free radicals, that may otherwise contribute to TAA degradation, is contemplated. Examples of suitable antioxidants include, for example, citric acid, ascorbic acid (vitamin C), tocopherols and tocotrienols (vitamin E), vitamin K, fumaric acid, malic acid, lactic acid, oxalic acid, and glutathione. Accordingly, the therapeutic compositions may also comprise an antioxidant. Preferably, the antioxidant acts as a reducing agent or oxygen scavenger. In one embodiment, the compositions comprise an antioxidant selected from the group consisting of oxalic acid, citric acid, ascorbic acid, fumaric acid, malic acid, lactic acid, and combinations thereof. In another embodiment, the compositions comprise an antioxidant selected from the group consisting of citric acid, ascorbic acid, fumaric acid, and combinations thereof. In another embodiment, the compositions comprise an antioxidant selected from the group consisting of ascorbic acid, fumaric acid, and combinations thereof. In a particularly preferred embodiment, the compositions comprise ascorbic acid.

Components such as acids or bases can also be added to adjust the pH of the compositions of the invention. Preferably, these compositions have a pH of less than 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, or 4.0. Acids which may be included in the compositions include: citric acid, ascorbic acid, fumaric acid, malic acid, and lactic acid.

In one embodiment of the present invention, the base material of the formulation comprises a mixture of from about 3 to 15 wt. % GANTREZ™ MS-955, from about 40 to 60 wt. % PEG 400, and from about 20 to 50 wt. % PEG 3350. The active ingredients of the composition comprise from about 0.01 to about 0.3 wt. %, and most preferably from about 0.01 to 0.25 wt. % triamcinolone acetonide, and from about 0.25 to 6 wt. %, most preferably from about 1.5 to 2.5 wt. % lidocaine or a salt thereof. Any reference herein to a weight percentage of lidocaine salt is based upon the molar equivalent of lidocaine free base. Therefore, a composition of the invention including 5.0 wt. % lidocaine free base would be formulated with 6.0 wt. % lidocaine hydrochloride. Such compositions, when applied to an aphthous ulcer in the oral cavity, are found to adhere well to the mucosal surface and to dissolve slowly in the saliva such that the medicament is delivered and the treatment maintained for a period of 15 minutes or longer. In comparison therewith, compositions based only on the PEG ointment without the GANTREZ™ copolymer component do not adhere well to the applied surface, dissolve more rapidly in the saliva, and are effective for a period of only a few minutes.

In another embodiment, the therapeutic composition contains about 0.1 wt. % triamcinolone acetonide, about 2.5 wt. % lidocaine hydrochloride, and a base material comprising from about 3 to 15 wt. % of a water soluble salt of a copolymer of a lower alkyl vinyl ether and maleic acid or anhydride and from about 85 to 97 wt. % of polyalkylene glycol, and in particular PEG.

In another embodiment, the therapeutic composition contains polyethylene glycol 400, polyethylene glycol 3350, a water soluble salt of a copolymer of a lower alkyl vinyl ether and maleic acid or anhydride, lidocaine or a salt thereof, triamcinolone acetonide, methylparaben, and propylparaben.

In yet another embodiment, the therapeutic composition contains about 52.6 wt. % polyethylene glycol 400, about 39.0 wt. % polyethylene glycol 3350, about 6.0 wt. % water soluble salt of a copolymer of a lower alkyl vinyl ether and maleic acid or anhydride, about 2.3 wt. % lidocaine hydrochloride, about 0.1 wt. % triamcinolone acetonide, about 0.2 wt. % methylparaben, and about 0.02 wt. % propylparaben.

In one embodiment, the therapeutic composition contains about 52.6 wt. % polyethylene glycol 400, about 39.0 wt. % polyethylene glycol 3350, about 6.0 wt. % water soluble salt of a copolymer of a lower alkyl vinyl ether and maleic acid or anhydride, about 2 wt. % lidocaine hydrochloride, about 0.1 wt. % triamcinolone acetonide, about 0.2 wt. % methylparaben, about 0.02 wt. % propylparaben, up to about 0.02 wt. % butylated hydroxytoluene, and up to about 0.01 wt. % butylated hydroxyanisole.

In yet another embodiment, the therapeutic composition is a composition, preferably an ointment composition, for the treatment of mouth sores comprising a polyalkylene glycol, a water soluble salt of a copolymer of a lower alkyl vinyl ether and maleic acid or anhydride, lidocaine hydrochloride, triamcinolone acetonide, and a preservative. In a particular embodiment, the composition for the treatment of mouth sores comprises polyethylene glycol 400, polyethylene glycol 3350, a water soluble salt of a copolymer of a lower alkyl vinyl ether and maleic acid or anhydride, lidocaine hydrochloride, triamcinolone acetonide, methylparaben, and propylparaben. The composition may comprise about 0.01 to about 0.3 wt. % triamcinolone acetonide, about 0.01 to about 0.25 wt. % triamcinolone acetonide, or about 0.075 to about 0.125 wt. % triamcinolone acetonide. In a particularly preferred embodiment, the therapeutic composition comprises about 0.1 wt. % triamcinolone acetonide.

The therapeutic composition may also comprise about 0.25 to about 6 wt. % lidocaine hydrochloride, about 0.25 to about 5 wt. % lidocaine hydrochloride, about 1 to about 5 wt. % lidocaine hydrochloride, or about 1.5 to about 2.5 wt. % lidocaine hydrochloride. In a particularly preferred embodiment, the therapeutic composition comprises 2 wt. % lidocaine hydrochloride. In an even more particularly preferred embodiment, the therapeutic composition comprises about 0.1 wt. % triamcinolone acetonide and about 2 wt. % lidocaine hydrochloride.

Method of Use

While the compositions of the present invention are particularly useful in the treatment of aphthous ulcers, the utility of the compositions is not so limited. The compositions of the present invention may also be used in the topical application of medicaments to other mucous membranes in nasal, rectal and vaginal applications as well as oral applications. In addition, the compositions of the present invention may be used in the general treatment of wounds, abrasions and other epidermal conditions where topical medicaments commonly find application. The compositions of the present invention are also useful for the treatment of eczema, bug bites, burns in mouth and, external mouth sores. The clinical efficacy of TAA and lidocaine containing formulations is known from the Repka patents and bioadhesive formulations prepared according to the Repka patent.

Method of Production

Stability of TAA may also be increased by reducing the amount of oxygen introduced into the formulation during production or packaging. This can be achieved in a number of ways, including, for example, by the production of any of the therapeutic compositions disclosed herein under an inert atmosphere. In one embodiment, the base material is mixed with the TAA and lidocaine or a salt thereof, under an inert atmosphere. The base may be purchased or produced as described herein.

In one embodiment, the base is produced by:

mixing a liquid polyalkylene glycol, preferably polyethylene glycol, a solid polyalkylene glycol, preferably polyethylene glycol, and a water soluble salt of a copolymer of a lower alkyl vinyl ether and maleic acid or anhydride at a temperature at or above the melting point of the solid polyethylene glycol to produce a homogenized mixture; and mixing a preservative, preferably methylparaben or propylparaben or a mixture of methylparaben and propylparaben with the homogenized mixture to form the base material.

In one embodiment, butylated hydroxytoluene (BHT), and/or butylated hydroxyanisole (BHA) may be added with the methylparaben and propylparaben to produce the base.

In another embodiment, the liquid PEG is PEG having a molecular weight of less than 600 such as PEG 400, and the solid PEG is PEG having a molecular weight above 600, such as PEG 3350.

In an embodiment, the base material and/or the homogenized mixture is produced under an inert atmosphere. In another embodiment, the composition is packaged under an inert atmosphere. The inert atmosphere comprises nitrogen, helium, or any inert gas or inert mixture of gases as known in the art. In a preferred embodiment, the inert atmosphere is nitrogen gas.

It is advantageous to add the active ingredients last because it reduces their exposure to oxygen and heat which could degrade the active ingredients. Furthermore, once it was discovered that lidocaine hydrochloride increased the stability of TAA in the formulation it became preferable to avoid dissolving the lidocaine hydrochloride in the PEG during the first step of base material production, as was described in the Repka patents, in order to increase shelf life of the composition.

In a preferred embodiment, a composition of the invention is prepared by first adding the liquid PEG into a homogenizer or other suitable mixer as known in the art. In one embodiment, the homogenizer is bottom fed and is under continuous vacuum to further minimize oxygen within the homogenizer. The liquid PEG is heated to a temperature at or above the melting temperature of the solid PEG. The solid PEG and the water soluble salt of a copolymer of a lower alkyl vinyl ether and maleic acid or anhydride (such as Gantrez™ MS-955) are then fed into the homogenizer and mixed with the liquid PEG until the solid PEG dissolves. Optionally, other solid components (such as methyl paraben, propyl paraben, BHA, or BHT) are then added to the homogenized mixture and well mixed. The base material is then cooled to about 55° C. Active ingredients, such as TAA and lidocaine or a salt thereof, are added to the cooled base material and well mixed to form the therapeutic composition. The composition is then further cooled and packaged. In one embodiment, the base material is prepared in an inert atmosphere.

Packaging

The stability of the present formulations may also be increased by packaging the formulations, preferably under an inert atmosphere, in containers designed to reduce the degradation of the TAA. Without being bound by a particular theory, it is believed that reduced exposure to oxygen increases the stability of the present formulations. As such, packaging that is designed or able to limit the amount of oxygen to which the formulations are exposed when contained therein is contemplated.

As the formulations are typically in the form of an ointment or gel, any conventional packaging that reduces exposure of the ointment or gel to oxygen, such as, for example, an oxygen impermeable container, but which also allows for dispensing or application of the ointment or gel is contemplated. Examples of such packaging include containers constructed of glass, plastic, metal, and in particular metal foil, or any combination thereof, or containers having a metal overwrap. In a particular embodiment, the ointment or gel is packaged in a flexible oxygen impermeable container such as a conventional metal foil container allowing for dispensing or application of the ointment or gel by the application of pressure to the container. In another embodiment, the container is wrapped in a metal overwrap or placed in a foil-lined or foil pouch such as Kapak VWR 2004/2005 Cat#11213-852.

Stability Analysis

The storage stability of a composition of the invention can be determined by measuring the concentration of TAA, lidocaine or a salt thereof, or degradation products of formulae I, II and III as described in Example 3. For example, the concentration of TAA, lidocaine or a salt thereof, or degradation products of formulae I, II and III can be measured by liquid chromatography using methods well known in the art. One method measures the concentration of TAA, lidocaine or a salt thereof, or degradation products of formulae I, II, and III by reverse phase high pressure liquid chromatography. The instrument parameters used to measure the experimental stability of TAA, lidocaine or a salt thereof, or degradation products of formulae I, II and III are set out below.

Instrument Parameters

| | |
|---|---|
| Injector | Hewlett Packard 1050 or 1100 Series |
| Pump | Hewlett Packard 1050 or 1100 Series |
| Detector | Hewlett Packard 1050 or 1100 Series |
| Software | Hewlett Packard Chemstation or Equivalent |
| Column | Agilent C8, zorbax, 3.5μ, 4.6 × 150 mm |
| Column Temperature | 30° C. |
| Wavelength | 238 nm and 280 nm (at 7.8 min) |
| Flow Rate | 1.2 mL/min |
| Injection Volume | 60 μL |
| Mobile Phase A | 0.05% TFA in DI water |
| Mobile Phase B | 0.05% TFA in Acetonitrile |

| | Time (min) | Mobile Phase | |
|---|---|---|---|
| Gradient | 0 min | 85% A | 15% B |
| | 11 min | 0% A | 100% B |
| | 13 min | 0% A | 100% B |
| | Post time 2 min | | |

Elution Time = Lidocaine (3.777 min), Methylparaben (5.161 min), formulae II (6.109 min), formulae I (5.881 min), TAA (6.316 min), formulae III (6.803 min), Propylparaben (6.990 min), BHA (8.488 min), BHT (11.774 min)

The storage stability of a therapeutic composition as disclosed herein may be determined by measuring the concentration of TAA, lidocaine or a salt thereof, or degradation products of formulae I, II, and III after exposure of the therapeutic composition to standard storage conditions. Typically, standard stability storage conditions comprise storage conditions in which the temperature is about room temperature and the relative humidity is generally about 60%. The International Conference on Harmonization (INC) guidelines dictate standard stability storage conditions to be at a temperature of 25° C.±2° C. and at a relative humidity of 60%±5%. A particularly preferred standard stability storage condition is at a temperature of about 25° C. and a relative humidity of about 60%. Once the particular conditions are selected, the composition is then subject to the standard stability conditions for a period of time sufficient to determine the effects of the conditions on the tested composition. By way of example, the therapeutic compositions disclosed herein may be subjected to the standard stability storage conditions for a period of time sufficient to determine the point at which the concentration of certain active ingredients falls below an acceptable concentration or when the concentration of an undesirable degradant exceeds an acceptable concentration. This period of time may be anywhere from a 6 month period, a 12 month period, an 18 month period, a 24 month period, a 30 month period, or even a 36 month period. It may also include any period in between, including, for example 7, 8, 9, 10, 11, 13, 14, 15, 16, 17, 19, 20, 21, 22, 23, 25, 26, 27, 28, 29, 31, 32, 33, 34, or 35 month periods.

Thus, in some embodiments, the therapeutic composition is a storage stable therapeutic composition having wet adherent properties comprising a base material, about 0.01 to about 0.3 wt. % triamcinolone acetonide, and about 0.25 to about 5 wt. % lidocaine or a salt thereof, the base material comprising from about 3 to 15 wt. % of a water soluble salt of a copolymer of a lower alkyl vinyl ether and maleic acid or anhydride and from about 85 to 97 wt. % of polyethylene glycol and having particular characteristics as determined by exposure to particular standard stability storage conditions. In particular, the storage stable therapeutic composition may comprise at least about 85% and preferably at least about 90%, 91%, 92%, 93%, 94%, 95%, 96%, 97%, 98%, and 99% of the amount of triamcinolone acetonide based on the amount of triamcinolone acetonide within the composition at the time of manufacture or about 85% and preferably at least about 90%, 91%, 92%, 93%, 94%, 95%, 96%, 97%, 98%, and 99% of the amount of lidocaine or a salt thereof based on the amount of lidocaine or salt thereof within the composition at the time of manufacture after about 12, preferably about 18, more preferably about 24, even more preferably about 30, and most preferably about 36 months, and in particular at standard stability storage conditions of 25° C.±2° C. and 60%±5% relative humidity, and in particular, standard stability storage conditions of 25° C. and 60% relative humidity. In particularly preferred embodiments, the storage stable therapeutic composition having wet adherent properties comprises a base material, about 0.01 to about 0.3 wt. % triamcinolone acetonide, and about 0.25 to about 6 wt. % lidocaine or a salt thereof, the base material comprising from about 3 to 15 wt. % of a water soluble salt of a copolymer of a lower alkyl vinyl ether and maleic acid or anhydride and from about 85 to 97 wt. % of polyethylene glycol, wherein (a) the composition comprises at least 90% of triamcinolone acetonide based on the amount of triamcinolone acetonide within the composition at the time of manufacture after 14 months storage at 25° C. and 60% relative humidity or (b) the composition comprises no more than about 10% of compounds having the formulae I, II, and III based upon the amount of triamcinolone acetonide within the composition at the time of manufacture after 14 months storage at 25° C. and 60% relative humidity.

In another embodiment, the therapeutic composition is a storage stable therapeutic composition having wet adherent properties comprising a base material, about 0.01 to about 0.3 wt. % triamcinolone acetonide, and about 0.25 to about 6 wt. % lidocaine or a salt thereof, the base material comprising from about 3 to 15 wt. % of a water soluble salt of a copolymer of a lower alkyl vinyl ether and maleic acid or anhydride and from about 85 to 97 wt. % of polyethylene glycol and having particular characteristics as determined by exposure to particular standard stability storage conditions. In particular, the storage stable therapeutic composition may comprise at least about 0.01 wt. % and preferably at least about 0.05 wt. %, 0.075 wt. %, 0.1 wt. %, 0.125, 0.15 wt. %, 0.2 wt. %, 0.25 wt. %, 0.3 wt. % triamcinolone acetonide and about 0.25 wt. % and preferably about 0.5 wt. %, 0.75 wt. %, 1 wt. %, 1.25 wt. %, 1.5 wt. %, 1.75 wt. %, 2 wt. %, 2.25 wt. %, 2.5 wt. %, 2.75 wt. %, 3 wt. %, 3.25 wt. %, 3.5 wt. %, 3.75 wt. %, 4 wt. %, 4.25 wt. %, 4.5 wt. %, 4.75 wt. %, 5 wt. %, 5.25 wt. %, 5.5 wt. % or 5.75 wt. % lidocaine or a salt thereof after about 12, preferably about 18, more preferably about 24, even more preferably about 30, and most preferably about 36 months, and in particular at standard stability storage conditions of 25° C.±2° C. and at a relative humidity of 60%±5%, and in particular standard stability storage conditions of 25° C. and 60% relative humidity. In a particularly preferred embodiment, the storage stable therapeutic composition having wet adherent properties comprises a base material, about 0.01 to about 0.3 wt. % triamcinolone acetonide, and about 0.25 to about 5 wt. % lidocaine or a salt thereof, the base material comprising from about 3 to 15 wt. % of a water soluble salt of a copolymer of a lower alkyl vinyl ether and maleic acid or anhydride and from about 85 to 97 wt. % of polyethylene glycol, wherein: (a) the composition comprises at least 0.09 wt. % triamcinolone acetonide and 1.8 wt. % lidocaine, and preferably 1.9 wt % lidocaine, or a salt thereof after 14 months or (b) the composition comprises no more than about 0.01 wt. % of compounds having the formulae I, II and III after 14 months.

In one embodiment, the therapeutic composition maintains a minimum TAA concentration of 0.09 wt. % for at least 14 months. Preferably, the composition maintains a minimum TAA concentration of 0.09 wt. % for at least 15, 16, 17, 18, 19, 20, 21, 22, 23, 24, 25, 26, 27, 28, 29, 30, 31, 32, 33, 34, 35, or 36 months or more. In one embodiment, the therapeutic composition has a maximum TAA concentration of 0.15% and a minimum TAA concentration of 0.09 wt. % for at least 14 months.

The storage stability of a therapeutic composition as disclosed herein may also be determined by measuring the concentration of TAA, lidocaine or a salt thereof, or degradation products of formulae I, II, and III after exposure of the therapeutic composition to accelerated stability storage conditions. Typically, accelerated stability storage conditions comprise storage conditions in which the temperature is in excess of room temperature and the relative humidity is in excess of 60%. The International Conference on Harmonization (IHC) guidelines dictate accelerated stability storage conditions to be at a temperature of 40° C.±2° C. and at a relative humidity of 75%±5%. A particularly preferred accelerated stability storage condition is at a temperature of about 40° C. and a relative humidity of about 75%. Once the particular conditions are selected, the composition is then subject to the accelerated stability conditions for a period of time sufficient to determine the effects of the conditions on the tested composition. By way of example, the therapeutic compositions disclosed herein may be subject to the accelerated stability storage conditions for a period of time sufficient to determine the point at which the concentration of certain active ingredients falls below an acceptable concentration or when the concentration of an undesirable degradant exceeds an acceptable concentration. This period of time may be anywhere from a one month period to a 6 month period, a 12 month period, an 18 month period, or even a 24 month period. It may also include any period in between, including, for example 2, 3, 4, 5, 7, 8, 9, 10, 11, 13, 14, 15, 16, 17, 19, 20, 21, 22, and 23 month periods.

Thus, in one embodiment, the therapeutic composition is a storage stable therapeutic composition having wet adherent properties comprising a base material, about 0.01 to about 0.3 wt. % triamcinolone acetonide, and about 0.25 to about 6 wt. % lidocaine or a salt thereof, the base material comprising from about 3 to 15 wt. % of a water soluble salt of a copolymer of a lower alkyl vinyl ether and maleic acid or anhydride and from about 85 to 97 wt. % of polyethylene glycol and having particular characteristics as determined by exposure to particular accelerated stability storage conditions. In particular, the storage stable therapeutic composition may comprise at least about 85%, preferably at least about 90%, still more preferably at least about 95%, even more preferably about 97%, and most preferably about 99% of the amount of triamcinolone acetonide based on the amount of triamcinolone acetonide within the composition at the time of manufacture or and about 85%, preferably at least about 90%, still more preferably at least about 95%, even more preferably about 97%, and most preferably about 99% of the amount of lidocaine or a salt thereof based on the amount of lidocaine or salt thereof within the composition at the time of manufacture after about 6, preferably about 12, more preferably about 18, and most preferably about 24 months of accelerated stability storage conditions of 40° C.±2° C. and 75±5% relative humidity, and in particular, accelerated stability storage conditions of 40° C. and 75% relative humidity. In a particularly preferred embodiment, the storage stable therapeutic composition having wet adherent properties comprises a base material, about 0.01 to about 0.3 wt. % triamcinolone acetonide, and about 0.25 to about 5 wt. % lidocaine or a salt thereof, the base material comprising from about 3 to 15 wt. % of a water soluble salt of a copolymer of a lower alkyl vinyl ether and maleic acid or anhydride and from about 85 to 97 wt. % of polyethylene glycol, wherein (a) the composition comprises at least 90% of said triamcinolone acetonide based upon the amount of said triamcinolone acetonide within the composition at the time of manufacture after 6 months accelerated stability storage at 40° C. and 75% relative humidity; or (b) the composition comprises no more than about 10% of the compounds having the formulae I, II, and III based upon the amount of said triamcinolone acetonide within the composition at the time of manufacture after 6 months accelerated stability storage at 40° C. and 75% relative humidity.

The disclosure of the Repka patents, U.S. Pat. Nos. 5,112,620 and 5,714,165, are incorporated by reference herein in their entirety.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1: Stability Tests for Formulations Containing TAA Only and TAA and Lidocaine Stability tests were conducted to determine the stability of TAA in a base material with wet adherent properties. The tests were conducted under accelerated and standard storage conditions.

Tests were conducted on formulation comprising a base material and TAA. The first formulation was identified as Formulation A and comprised the raw materials listed in the table below.

Formulation A

| Raw Material | % of Product by Wt. |
| --- | --- |
| Polyethylene Glycol (PEG) 400 | 53.7% |
| Polyethylene Glycol (PEG) 3350 | 39.9% |
| Gantrez ™ MS-955 | 6.0% |
| Methylparaben | 0.2% |
| Triamcinolone Acetonide (TAA) | 0.1% |
| Edetate Disodium, Dihydrate | 0.05% |
| Propylparaben | 0.02% |
| Butylated Hydroxytoluene (BHT) | 0.02% |
| Butylated Hydroxyanisole (BHA) | 0.01% |
| Total | 100% |

Formulation A was produced on a production scale, the formulation was prepared by first adding the PEG 400 into a Ross VersaMix kettle. The PEG 3350 was then added and the mixture heated with mixing to 60-65° C. The PEGs were mixed at this temperature for 10 minutes. The BHA, BHT, propyl paraben, and methyl paraben were added to the kettle and the mixture maintained at 60-65° C. with mixing for 10 minutes. The EDTA and Gantrez™ MS-955 were then added and the heated mixture was then stirred an additional 10 minutes. TAA was then added and the mixture was maintained at 60-65° C. with mixing for 10 minutes. The formulation was then cooled to 44-54° C., deaerated via vacuum, and packaged for storage.

The results of the stability studies for formulation A are summarized in the tables below.

TABLE 1a

Accelerated Storage (40° C./75% relative humidity)

| Months of Storage | Measured % of theoretical concentration |
| --- | --- |
| Initial Preparation | 100.8 |
| 1 | 96.5 |
| 2 | 93.0 |
| 3 | 87.9 |
| 6 | 78.7 |

TABLE 1b

Room Temperature Storage (25° C./60% relative humidity)

| Months of Storage | Measured % of theoretical concentration |
| --- | --- |
| Initial Preparation | 100.8 |
| 3 | 97.1 |
| 6 | 95.2 |
| 9 | 89.2 |
| 12 | 84.2 |

The stability tests were repeated on a formulation comprising a base material, TAA, and lidocaine. The formulation was identified as Formulation B and comprised the raw materials listed in the table below.

Formulation B

| Raw Material | % of Product by Wt. |
| --- | --- |
| Polyethylene Glycol (PEG) 400 | 52.6 |
| Polyethylene Glycol (PEG) 3350 | 39.0 |
| Gantrez ™ MS-955 | 6.0 |
| Lidocaine (LID) | 2.0 |
| Methylparaben | 0.2 |
| Triamcinolone Acetonide (TAA) | 0.1 |
| Edetate Disodium, Dihydrate | 0.05 |
| Propylparaben | 0.02 |
| Butylated Hydroxytoluene (BHT) | 0.02 |
| Butylated Hydroxyanisole (BHA) | 0.01 |
| Total | 100% |

Formulation B was produced on a production scale, the formulation was prepared by first adding the PEG 400 into a Ross VersaMix kettle. The PEG 3350 was then added and the mixture heated with mixing to 60-65° C. The PEGs were mixed at this temperature for 10 minutes. The BHA, BHT, propyl paraben, and methyl paraben were added to the kettle and the mixture maintained at 60-65° C. with mixing for 10 minutes. The EDTA and Gantrez™ MS-955 were then added and the heated mixture was then stirred an additional 10 minutes. TAA and lidocaine were then added and the mixture was maintained at 60-65° C. with mixing for 10 minutes. The formulation was then cooled to 44-54° C., deaerated via vacuum, and packaged for storage.

The results of the test for formulation B are summarized in the tables below.

TABLE 2a

Accelerated (40° C./75% relative humidity)

| Months of Storage | Measured % of theoretical concentration |
|---|---|
| Initial Preparation | 100.4 |
| 1 | 96.8 |
| 2 | 94.3 |
| 3 | 92.9 |
| 6 | 82.2 |

TABLE 2b

Room Temperature (25° C./60% relative humidity)

| Months of Storage | Measured % of theoretical concentration |
|---|---|
| Initial Preparation | 100.4 |
| 3 | 96.5 |
| 6 | 96.1 |
| 9 | 93.9 |
| 12 | 90.4 |

The data in table 1 b shows Formulation A would fail the FDA shelf life storage stability requirement for TAA between 6 and 9 months of storage under standard storage conditions. Extrapolation of the data in table 2b shows formulation B's TAA concentration would fail after 13 months. Comparison of Formulation A and B, surprisingly, shows that the addition of lidocaine had a stabilizing effect.

Example 2: Stability Tests for Formulations Containing Various Forms of Lidocaine Five formulations were prepared and tested to determine the effect of lidocaine and lidocaine hydrochloride in formulations comprising a base material and TAA.

Each formulation was prepared on a laboratory scale. The dry ingredients, including active ingredients, were added to a 1 L beaker and mixed well with a mechanical stirrer for thirty minutes. The PEG 400 was added to the beaker with continuous stirring and heating to 65° C. over a period of thirty minutes to form a hot gel. The hot gel was then transferred into 11 glass vials and allowed to cool to room temperature.

The five formulations contained varying combinations of lidocaine, lidocaine hydrochloride, and TAA, as well as benzoic acid to lower the pH of the formulations. The components of each formulation are summarized in the tables below.

Formulation A (Only TAA)

| Raw Material | % of Product by Wt. |
|---|---|
| Polyethylene Glycol (PEG) 400 | 53.7% |
| Polyethylene Glycol (PEG) 3350 | 39.9% |
| Gantrez ™ MS-955 | 6.0% |
| Methylparaben | 0.2% |
| Triamcinolone Acetonide (TAA) | 0.1% |
| Edetate Disodium, Dihydrate | 0.05% |
| Propylparaben | 0.02% |
| Butylated Hydroxytoluene (BHT) | 0.02% |
| Butylated Hydroxyanisole (BHA) | 0.01% |
| Total | 100% |

Formulation B (TAA+Lid)

| Raw Material | % of Product by Wt. |
|---|---|
| Polyethylene Glycol (PEG) 400 | 52.6 |
| Polyethylene Glycol (PEG) 3350 | 39.0 |
| Gantrez ™ MS-955 | 6.0 |
| Lidocaine (LID) | 2.0 |
| Methylparaben | 0.2 |
| Triamcinolone Acetonide (TAA) | 0.1 |
| Edetate Disodium, Dihydrate | 0.05 |
| Propylparaben | 0.02 |
| Butylated Hydroxytoluene (BHT) | 0.02 |
| Butylated Hydroxyanisole (BHA) | 0.01 |
| Total | 100% |

Formulation C (Lid-Bz)

| Raw Material | % of Product by Wt. |
|---|---|
| Polyethylene Glycol (PEG) 400 | 52.9% |
| Polyethylene Glycol (PEG) 3350 | 38.3% |
| Gantrez ™ MS-955 | 6.0% |
| Lidocaine | 2.0% |
| Methylparaben | 0.2% |
| Triamcinolone Acetonide (TAA) | 0.1% |
| Edetate Disodium, Dihydrate | 0.05% |
| Propylparaben | 0.02% |
| Butylated Hydroxytoluene (BHT) | 0.02% |
| Butylated Hydroxyanisole (BHA) | 0.01% |
| Benzoic acid | 0.4% |
| Total | 100% |

Formulation D (Lid.HCl)

| Raw Material | % of Product by Wt. |
|---|---|
| Polyethylene Glycol (PEG) 400 | 52.3% |
| Polyethylene Glycol (PEG) 3350 | 38.8% |
| Gantrez ™ MS-955 | 6.0% |
| Lidocaine Hydrochloride (LID•HCl) | 2.5% |
| Methylparaben | 0.2% |
| Triamcinolone Acetonide (TAA) | 0.1% |
| Edetate Disodium, Dihydrate | 0.05% |
| Propylparaben | 0.02% |
| Butylated Hydroxytoluene (BHT) | 0.02% |
| Butylated Hydroxyanisole (BHA) | 0.01% |
| Total | 100% |

Formulation E (Lid.HCl+Bz)

| Raw Material | % of Product by Wt. |
|---|---|
| Polyethylene Glycol (PEG) 400 | 52.6% |
| Polyethylene Glycol (PEG) 3350 | 38.2% |
| Gantrez ™ MS-955 | 6.0% |
| Lidocaine Hydrochloride (LID•HCl) | 2.3% |
| Methylparaben | 0.20% |
| Triamcinolone Acetonide (TAA) | 0.1% |

-continued

| Raw Material | % of Product by Wt. |
|---|---|
| Edetate Disodium, Dihydrate | 0.05% |
| Propylparaben | 0.02% |
| Butylated Hydroxytoluene (BHT) | 0.02% |
| Butylated Hydroxyanisole (BHA) | 0.01% |
| Benzoic acid | 0.5% |
| Total | 100% |

The pH of the five formulations was measured. To determine the pH of each formulation approximately 1 g of sample was placed into a beaker and diluted with 50 mL of DI water. Two drops of a saturated solution of KCl were added and the pH was then measured using a calibrated pH meter. The results of the pH measurements are reported in the table below.

TABLE 3

| Formulation Identification Name | Components of formulation | pH |
|---|---|---|
| Formulation A (Only TAA) | No lidocaine, only TAA in the base formulation | 6.81 |
| Formulation B (TAA + Lid) | TAA + lidocaine in the base formulation | 8.10 |
| Formulation C (Lid-Bz) | TAA + lidocaine + benzoic acid in base formulation | 7.32 |
| Formulation D (Lid-HCl) | TAA + lidocaine hydrochloride in the base formulation | 6.79 |
| Formulation E (Lid-HCl + Bz) | TAA + lidocaine hydrochloride + benzoic acid in base formulation | 6.07 |

The formulations were stored under accelerated storage conditions as in Example 1. Periodic measurements were made to determine the concentration of TAA in the formulations.

Figure 2:
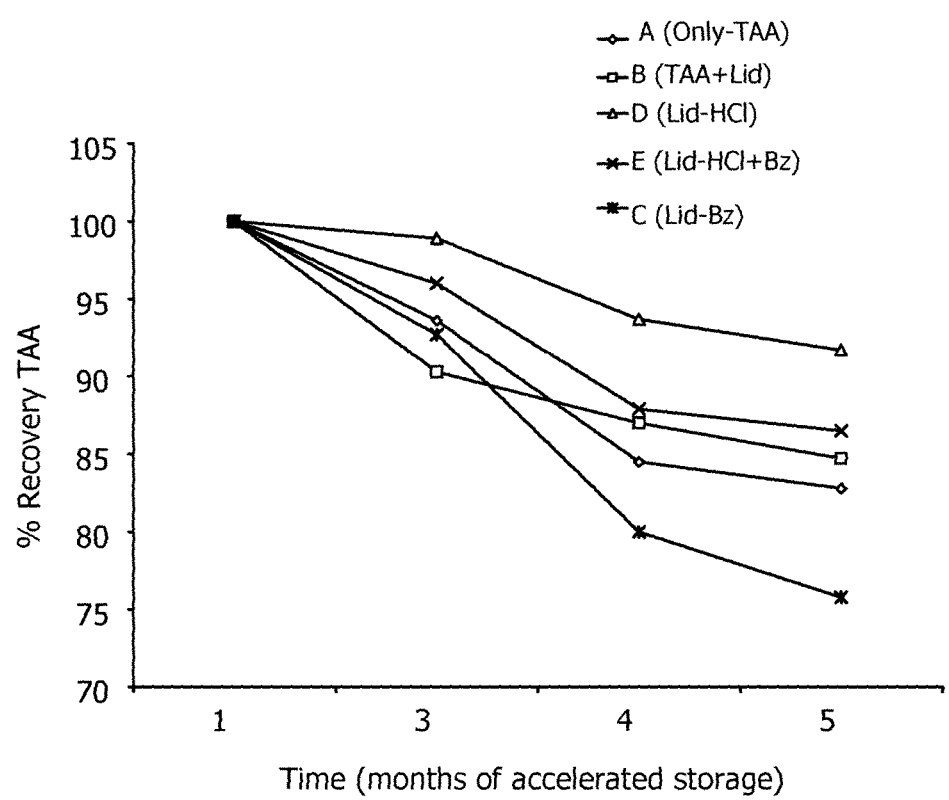
FIG. 2 is a graph depicting the normalized stability of TAA and lidocaine formulations as a percent recovery of TAA versus time as described in greater detail in the examples "macc" is months of accelerated storage.

The results of the five month accelerated storage test at 40° C. and 75% relative humidity are illustrated in Table 4A and 4B below and in FIGS. 1 and 2. The data contained in Tables 4A and 4B and in FIGS. 1 and 2 shows that the formulation with TAA and lidocaine hydrochloride (Lid-HCl) was the most stable formulation of TAA in the bioadhesive base.

TABLE 4A

TAA % after months of accelerated storage

| Formulation | 1 mo. | 3 mos. | 4 mos. | 5 mos. |
|---|---|---|---|---|
| A (Only-TAA) | 101.4 | 95 | 85.9 | 84.2 |
| B (TAA + Lid) | 103.2 | 93.5 | 90.2 | 87.9 |
| C (Lid-Bz) | 98 | 90.7 | 78 | 73.8 |
| D (Lid-HCl) | 101.6 | 100.5 | 95.3 | 93.3 |
| E (Lid-HCl + Bz) | 95.5 | 91.5 | 83.4 | 82 |

TABLE 4B

Normalized TAA % after months of accelerated storage

| Formulation | 1 mo. | 3 mos. | 4 mos. | 5 mos. |
|---|---|---|---|---|
| A (Only-TAA) | 100 | 93.6 | 84.5 | 82.8 |
| B (TAA + Lid) | 100 | 90.3 | 87 | 84.7 |
| C (Lid-Bz) | 100 | 92.7 | 80 | 75.8 |
| D (Lid-HCl) | 100 | 98.9 | 93.7 | 91.7 |
| E (Lid-HCl + Bz) | 100 | 96 | 87.9 | 86.5 |

By comparing formulation B (pH 8.10) to formulation C (pH 7.32) and formulation D (pH 6.79) to formulation E (pH 6.07) it is shown that TAA in a bioadhesive formulation is degraded faster in a formulation with acid added than in a formulation without acid added. Therefore, decreasing the pH of the bioadhesive formulation did not increase stability of TAA as reported by Gupta and Ungphaiboon for TAA solutions. It appears that the benzoic acid interfered with the stabilizing properties of lidocaine and lidocaine hydrochloride.

Example 3: Determination of Degradants

LC-MS studies have found the degradation of TAA in formulation B results in the formation of three key oxidative degradation compounds having the formulae:

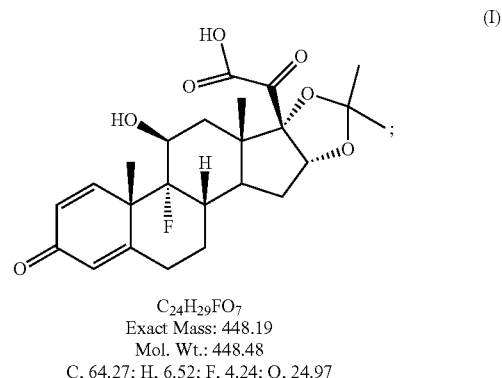

(I)

$C_{24}H_{29}FO_7$
Exact Mass: 448.19
Mol. Wt.: 448.48
C, 64.27; H, 6.52; F, 4.24; O, 24.97

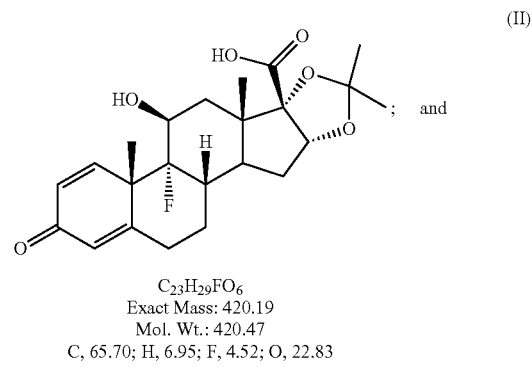

(II)

$C_{23}H_{29}FO_6$
Exact Mass: 420.19
Mol. Wt.: 420.47
C, 65.70; H, 6.95; F, 4.52; O, 22.83 and

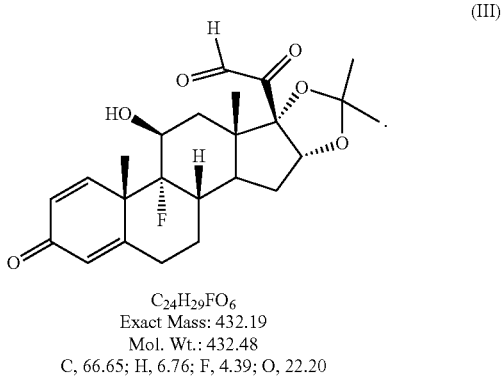

(III)

$C_{24}H_{29}FO_6$
Exact Mass: 432.19
Mol. Wt.: 432.48
C, 66.65; H, 6.76; F, 4.39; O, 22.20

These degradation products were found in both degraded TAA (degraded drug substance) and degraded formulation B (degraded drug product sample). HPLC chromatograms of these decomposed samples indicate that the combined peak areas of formulae I, II, and III correspond to the loss of area in the TAA peak due to oxidative degradation. Therefore, with due consideration of the margin of analytical error, mass balance can be achieved as the relative total area count of these three indicator compounds and can be used to monitor the stability of TAA in the formulation. International Conference on Harmonization (ICH) Guidance Document Q1A, "Stability Testing of New Drug Substances and Products."

Example 4: Air Oxidation of TAA-Lidocaine Hydrochloride and TAA-Lidocaine Free Base in a Mixture of Methanol and Water The purpose of this investigation was to demonstrate that formulation D, using lidocaine hydrochloride, is more stable to air exposure than formulation B, using lidocaine.

Experiment A—A solution of TAA (29 mg) in methanol (20 mL) was treated with lidocaine (580 mg), and air bubbled through the mixture using a glass pipette.

Experiment B—A solution of TAA (32 mg) in methanol (20 mL) was treated with lidocaine hydrochloride (640 mg) and air bubbled through the mixture using a glass pipette.

Figure 3:
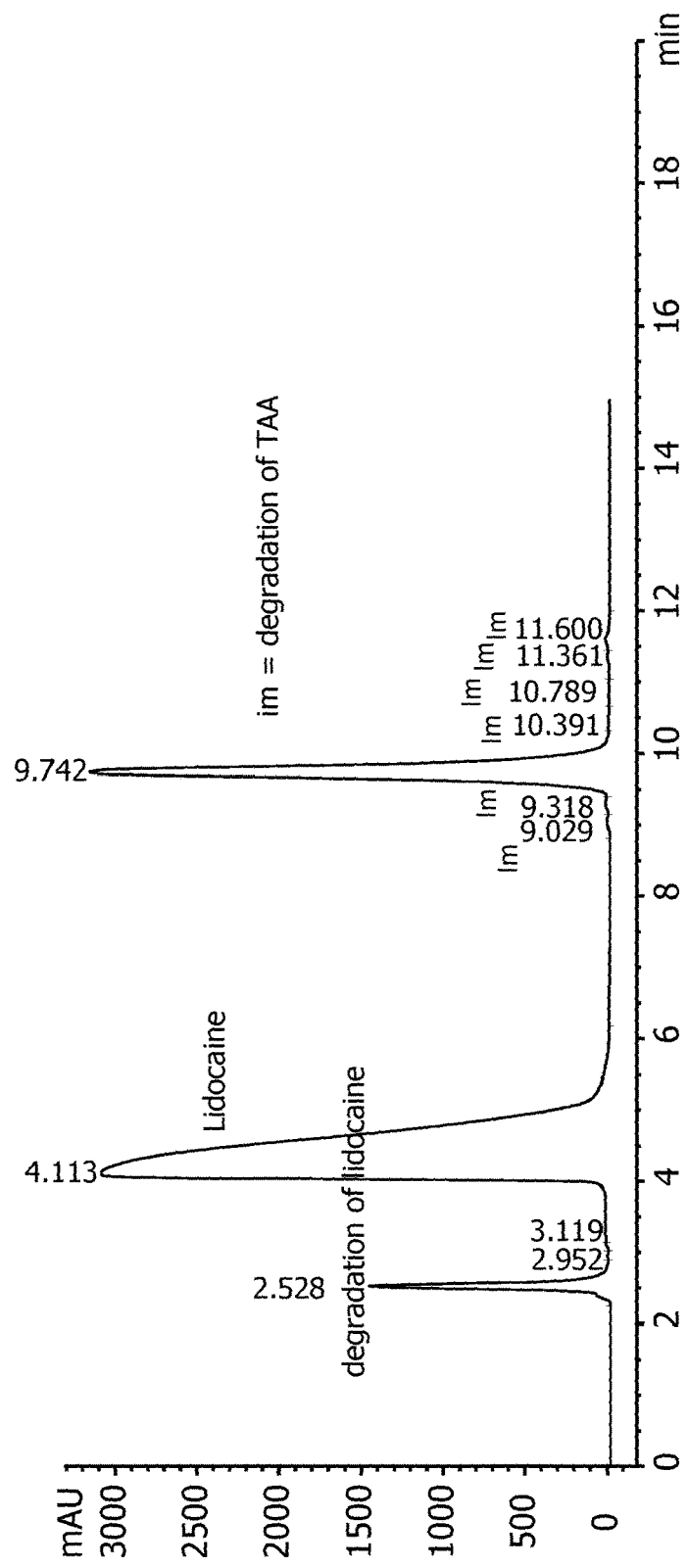
FIG. 3 is an HPLC chromatogram depicting the results of Experiment A as described in greater detail in the examples.
Figure 4:
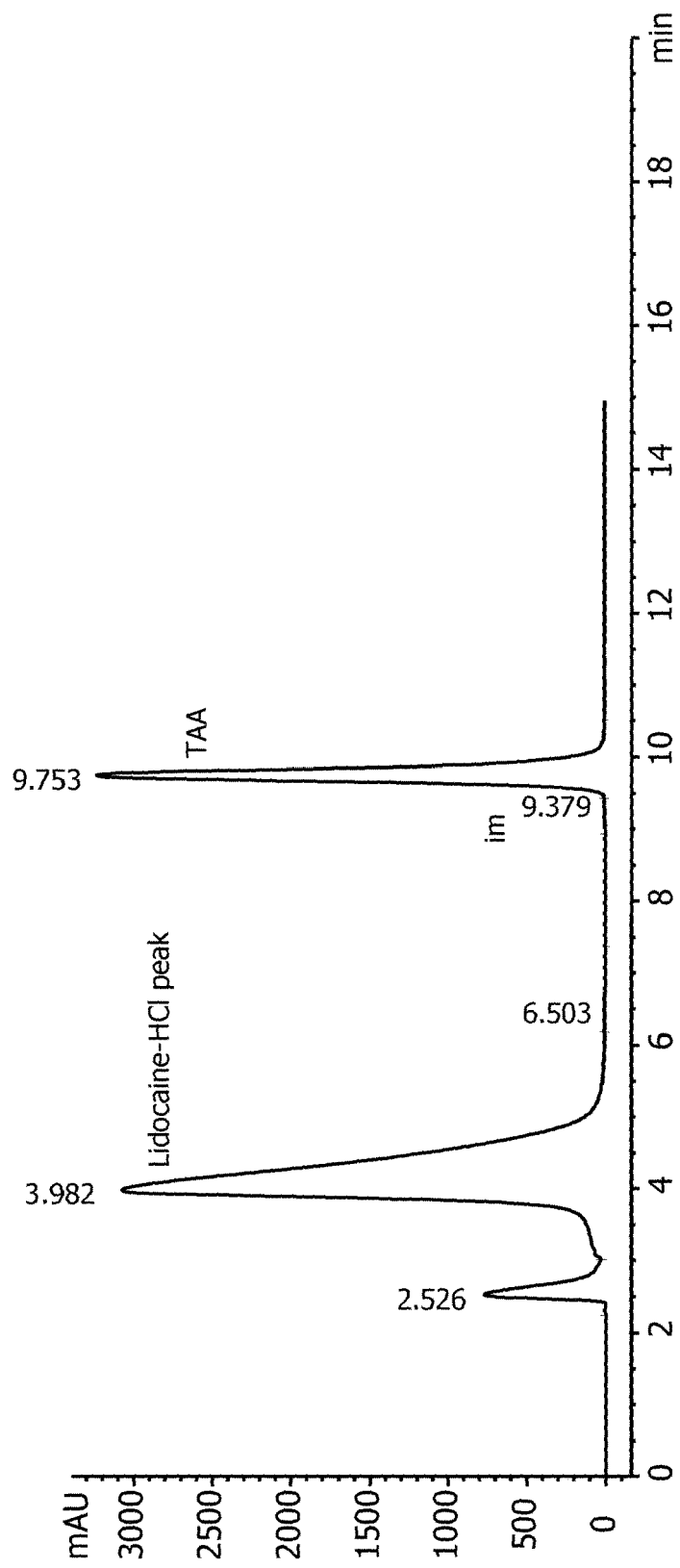
FIG. 4 is an HPLC chromatogram depicting the results of Experiment B as described in greater detail in the examples.

The progress of each experiment was monitored by HPLC. The HPLC results showed there was no significant difference between the experiments after 24 hrs. To each of these reactions was added water (1 mL) and the reaction was allowed to continue over two days. The HPLC results showed a significant difference between experiment A, illustrated as the HPLC chromatogram of FIG. 3, and experiment B, illustrated as the HPLC chromatogram of FIG. 4. Experiment A (TAA-Lidocaine) showed significant impurities (Im) versus experiment B (TAA-Lidocaine-hydrochloride).

The area of the TAA peak decreased as the experiment continued (data not shown). It was found that the increase in peak area of the impurities was directly proportional to the decrease of the TAA peak area.

Example 5: Stability of Formulations B and D Under Oxidative Stress Conditions In separate beakers 1.543 g of formulation B and 1.560 g of the formulation D were dissolved in methanol (20 mL). To these solutions was added copper(II) acetate (6.89 mg). In formulation B, the color of the solution changed from blue to green immediately. In formulation D, the color of the solution changed from blue to green only after heating for 5 min. The color of copper (II) is blue and the color of the copper (I) is green. This experiment shows formulation D is more resistant to oxidation than formulation B.

Example 6: Stability of Formulations B and D Under Oxidative Stress Conditions The purpose of this investigation is to determine the effects of individual ingredients such as EDTA, BHA, BHT, lidocaine free base, and lidocaine hydrochloride on the stability of TAA in the formulations listed in Table 5 and the specific Formulation Detail Tables listed thereafter. The method of preparation of the formulations is the same as listed in Method of Production above using pilot scale manufacturing equipment (5 kg scale).

TABLE 5

| Formulation ID | Formulation Constituents |
| --- | --- |
| 001 | Using Lidocaine free base |
| 002 | Using Lidocaine•HCl Monohydrate |
| 003 | Using Lidocaine•HCl Monohydrate |
| 004 | Using Lidocaine•HCl Monohydrate |
| 005 | Using Lidocaine•HCl Monohydrate minus BHA & BHT |
| 006 | Using Lidocaine•HCl Monohydrate minus EDTA |
| 007 | Using Lidocaine•HCl Monohydrate minus BHA/BHT/EDTA |
| 008 | Using Lidocaine•HCl Monohydrate minus BHA/BHT/EDTA |
| 009 | Using Lidocaine•HCl Monohydrate minus BHA/BHT/EDTA |
| 010 | Current Formulation, TAA only, minus LID |
| 011 | Current Formulation, TAA only, minus LID, BHA, BHT, EDTA |
| 012 | Using LID•HCl Monohydrate minus TAA |
| 013 | Using LID•HCl Monohydrate minus TAA, BHT/BHA, EDTA |
| 014* | Using LID•HCl Monohydrate with TAH, minus TAA, BHT/BHA, EDTA |
| 015* | Using LID•HCl Monohydrate minus BHT/BHA, EDTA, Plus Oxalic Acid |
| 016* | Using LID•HCl Monohydrate minus BHT/BHA, EDTA, Plus Citric Acid |
| 017 | Using LID•HCl Monohydrate minus BHT/BHA, EDTA, Plus Ascorbic Acid |
| 018 | Using LID•HCl Monohydrate minus BHT/BHA, EDTA, Plus Fumaric Acid |
| 019* | Using LID•HCl Monohydrate minus BHT/BHA, EDTA, Plus DL Malic Acid |
| 020* | Using LID•HCl Monohydrate minus BHT/BHA, EDTA, Plus Lactic Acid |

*study numbers 014-016, 019, and 020, as discussed in greater detail below, were not further examined.

Formulation Details
Formulation 001

| Raw Material | % of Product by Wt. |
| --- | --- |
| Polyethylene Glycol (PEG) 400 | 52.600 |
| Polyethylene Glycol (PEG) 3350 | 39.000 |
| GANTREZ ™ MS-955 | 6.000 |
| Lidocaine | 2.000 |
| Methylparaben | 0.200 |
| Triamcinolone Acetonide (TAA) | 0.100 |
| Edetate Disodium, Dihydrate | 0.050 |
| Propylparaben | 0.020 |
| Butylated Hydroxytoluene (BHT) | 0.020 |
| Butylated Hydroxyanisole (BHA) | 0.010 |
| Total | 100.000 |

Formulation 002-004

| Raw Material | % of Product by Wt. |
| --- | --- |
| Polyethylene Glycol (PEG) 400 | 52.312 |
| Polyethylene Glycol (PEG) 3350 | 38.823 |
| GANTREZ ™ MS-955 | 6.000 |
| Lidocaine•HCl (LID•HCl) | 2.465 |
| Methylparaben | 0.200 |
| Triamcinolone Acetonide (TAA) | 0.100 |
| Edetate Disodium, Dihydrate | 0.050 |
| Propylparaben | 0.020 |
| Butylated Hydroxytoluene (BHT) | 0.020 |
| Butylated Hydroxyanisole (BHA) | 0.010 |
| Total | 100.000 |

Formulation 005

| Raw Material | % of Product by Wt. |
| --- | --- |
| Polyethylene Glycol (PEG) 400 | 52.329 |
| Polyethylene Glycol (PEG) 3350 | 38.836 |

Formulation 006 (continued)

| Raw Material | % of Product by Wt. |
|---|---|
| GANTREZ ™ MS-955 | 6.000 |
| Lidocaine•HCl (LID•HCl) | 2.465 |
| Methylparaben | 0.200 |
| Triamcinolone Acetonide (TAA) | 0.100 |
| Edetate Disodium, Dihydrate | 0.050 |
| Propylparaben | 0.020 |
| Butylated Hydroxytoluene (BHT) | 0.000 |
| Butylated Hydroxyanisole (BHA) | 0.000 |
| Total | 100.000 |

Formulation 007-009

| Raw Material | % of Product by Wt. |
|---|---|
| Polyethylene Glycol (PEG) 400 | 52.341 |
| Polyethylene Glycol (PEG) 3350 | 38.844 |
| GANTREZ ™ MS-955 | 6.000 |
| Lidocaine•HCl (LID•HCl) | 2.465 |
| Methylparaben | 0.200 |
| Triamcinolone Acetonide (TAA) | 0.100 |
| Edetate Disodium, Dihydrate | 0.000 |
| Propylparaben | 0.020 |
| Butylated Hydroxytoluene (BHT) | 0.020 |
| Butylated Hydroxyanisole (BHA) | 0.010 |
| Total | 100.000 |

Formulation 010

| Raw Material | % of Product by Wt. |
|---|---|
| Polyethylene Glycol (PEG) 400 | 52.358 |
| Polyethylene Glycol (PEG) 3350 | 38.857 |
| GANTREZ ™ MS-955 | 6.000 |
| Lidocaine•HCl (LID•HCl) | 2.465 |
| Methylparaben | 0.200 |
| Triamcinolone Acetonide (TAA) | 0.100 |
| Edetate Disodium, Dihydrate | 0.000 |
| Propylparaben | 0.020 |
| Butylated Hydroxytoluene (BHT) | 0.000 |
| Butylated Hydroxyanisole (BHA) | 0.000 |
| Total | 100.000 |

Formulation 011

| Raw Material | % of Product by Wt. |
|---|---|
| Polyethylene Glycol (PEG) 400 | 53.748 |
| Polyethylene Glycol (PEG) 3350 | 39.852 |
| GANTREZ ™ MS-955 | 6.000 |
| Lidocaine | 0.000 |
| Methylparaben | 0.200 |
| Triamcinolone Acetonide (TAA) | 0.100 |
| Edetate Disodium, Dihydrate | 0.050 |
| Propylparaben | 0.020 |
| Butylated Hydroxytoluene (BHT) | 0.020 |
| Butylated Hydroxyanisole (BHA) | 0.010 |
| Total | 100.000 |

| Raw Material | % of Product by Wt. |
|---|---|
| Polyethylene Glycol (PEG) 400 | 53.794 |
| Polyethylene Glycol (PEG) 3350 | 39.886 |

Formulation 011 (continued)

| Raw Material | % of Product by Wt. |
|---|---|
| GANTREZ ™ MS-955 | 6.000 |
| Lidocaine | 0.000 |
| Methylparaben | 0.200 |
| Triamcinolone Acetonide (TAA) | 0.100 |
| Edetate Disodium, Dihydrate | 0.000 |
| Propylparaben | 0.020 |
| Butylated Hydroxytoluene (BHT) | 0.000 |
| Butylated Hydroxyanisole (BHA) | 0.000 |
| Total | 100.000 |

Formulation 012

| Raw Material | % of Product by Wt. |
|---|---|
| Polyethylene Glycol (PEG) 400 | 52.369 |
| Polyethylene Glycol (PEG) 3350 | 38.866 |
| GANTREZ ™ MS-955 | 6.000 |
| Lidocaine•HCl (LID•HCl) | 2.465 |
| Methylparaben | 0.200 |
| Triamcinolone Acetonide (TAA) | 0.000 |
| Edetate Disodium, Dihydrate | 0.050 |
| Propylparaben | 0.020 |
| Butylated Hydroxytoluene (BHT) | 0.020 |
| Butylated Hydroxyanisole (BHA) | 0.010 |
| Total | 100.000 |

Formulation 013

| Raw Material | % of Product by Wt. |
|---|---|
| Polyethylene Glycol (PEG) 400 | 52.415 |
| Polyethylene Glycol (PEG) 3350 | 38.900 |
| GANTREZ ™ MS-955 | 6.000 |
| Lidocaine•HCl (LID•HCl) | 2.465 |
| Methylparaben | 0.200 |
| Triamcinolone Acetonide (TAA) | 0.000 |
| Edetate Disodium, Dihydrate | 0.000 |
| Propylparaben | 0.020 |
| Butylated Hydroxytoluene (BHT) | 0.000 |
| Butylated Hydroxyanisole (BHA) | 0.000 |
| Total | 100.000 |

Formulation 017

| Raw Material | % of Product by Wt. |
|---|---|
| Polyethylene Glycol (PEG) 400 | 51.210 |
| Polyethylene Glycol (PEG) 3350 | 38.005 |
| GANTREZ ™ MS-955 | 6.000 |
| Lidocaine•HCl (LID•HCl) | 2.465 |
| Methylparaben | 0.200 |
| Triamcinolone Acetonide (TAA) | 0.100 |
| Edetate Disodium, Dihydrate | 0.000 |
| Propylparaben | 0.020 |
| Butylated Hydroxytoluene (BHT) | 0.000 |
| Butylated Hydroxyanisole (BHA) | 0.000 |
| Ascorbic Acid | 2.000 |
| Total | 100.000 |

Formulation 018

| Raw Material | % of Product by Wt. |
|---|---|
| Polyethylene Glycol (PEG) 400 | 51.210 |
| Polyethylene Glycol (PEG) 3350 | 38.005 |

-continued

| Raw Material | % of Product by Wt. |
|---|---|
| GANTREZ ™ MS-955 | 6.000 |
| Lidocaine•HCl (LID•HCl) | 2.465 |
| Methylparaben | 0.200 |
| Triamcinolone Acetonide (TAA) | 0.100 |
| Edetate Disodium, Dihydrate | 0.000 |
| Propylparaben | 0.020 |
| Butylated Hydroxytoluene (BHT) | 0.000 |
| Butylated Hydroxyanisole (BHA) | 0.000 |
| Fumaric Acid | 2.000 |
| Total | 100.000 |

Twenty bio-adhesive gel pilot batches, designated 001 through 020, were formulated. Formulation 001 contains Lidocaine free base. Formulations 002 to 004 contain Lidocaine Hydrochloride in place of the Lidocaine free base. Formulations 005 and 006 were designed to assess the roles of EDTA, BHA, and BHT. The formulation used in 007 to 009 was designed to assess the impact of removing all of these preservatives/anitoxidants. Trials 010 and 011 were designed to assess the impact of removing Lidocaine from the formulation completely to better understand the effect on the TAA. Formulations 012 and 013 established the impact of preservative/antioxidant removal on the Lidocaine stability. In addition they help to assess the presence of lidocaine degradation products in the absence of TAA. In Formulation 014, TAA was replaced with triamcinolone hexanoide (TH), a derivative of TAA, to assess TH stability versus TAA. Formulations 015 through 020 were designed to establish the effect of individual organic acids/antioxidants on the oxidative degradation of TAA.

Figure 5:
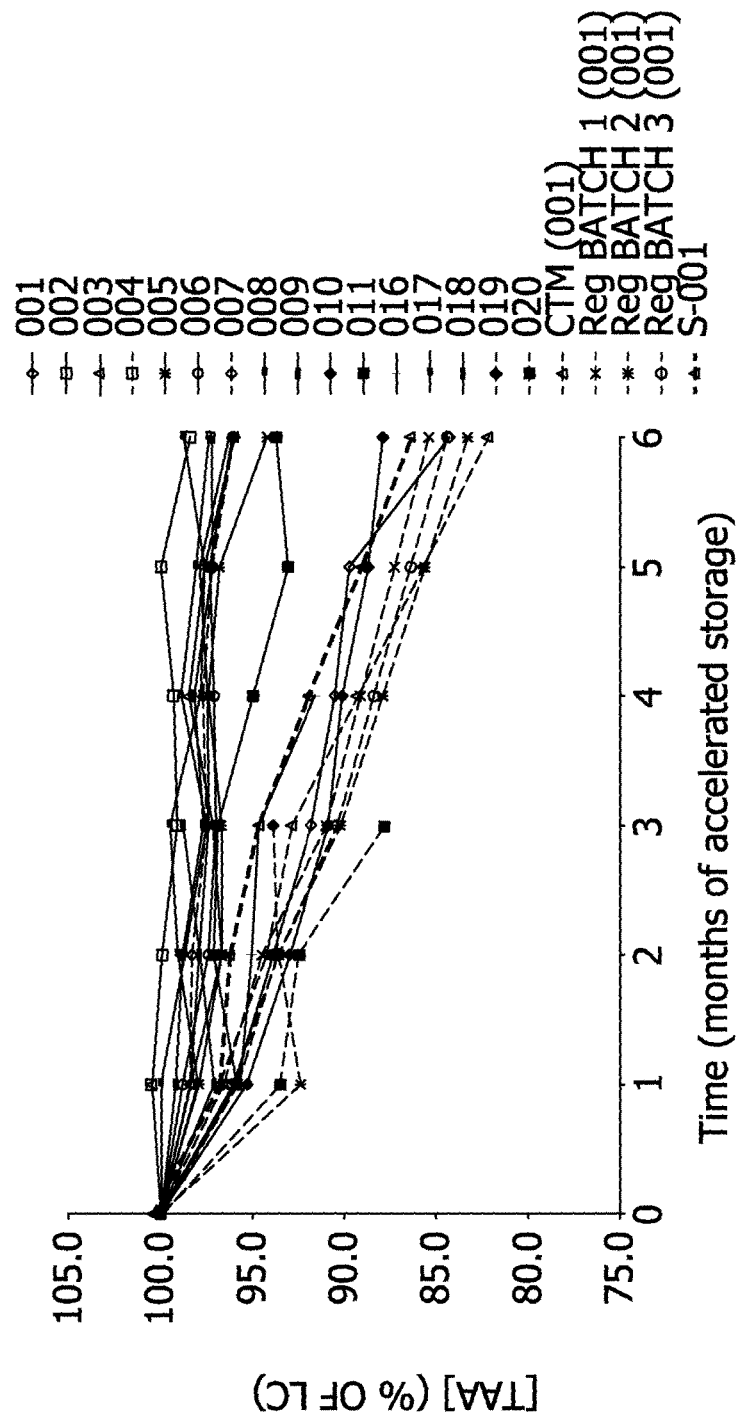
FIG. 5 is a graph depicting the stability of various TAA and lidocaine formulations as the concentration of TAA versus time under the accelerated storage conditions of 40° C. and 75% relative humidity (RH) as described in greater detail in Example 6.

Normalized TAA assay results for six months of accelerated stability storage are represented in Table 6 and in FIG. 5.

TABLE 6

Normalized TAA assay results for 6 months of accelerated stability storage

| Lot# | 0 m | 1 m | 2 m | 3 m | 4 m | 5 m | 6 m |
|---|---|---|---|---|---|---|---|
| 001 | 100 | 96 | 93.9 | 91.8 | 90.5 | 89.7 | 84.3 |
| 002 | 100 | 100.5 | 99.9 | 99.1 | 99.3 | 100 | 98.4 |
| 003 | 100 | 98.4 | 96.7 | 97.2 | 98.5 | 97.6 | 96.1 |
| 004 | 100 | 98.4 | 97.9 | 97.4 | 97.5 | 97.9 | 96.3 |
| 005 | 100 | 97.9 | 96.7 | 96.7 | 97.4 | 96.8 | 94.2 |
| 006 | 100 | 98.8 | 97.4 | 97.0 | 97.1 | 97.3 | 96.1 |
| 007 | 100 | 98.4 | 98.3 | 97.5 | 97.7 | 97.2 | 96.0 |
| 008 | 100 | 100 | 98.7 | 97.5 | 98.9 | 98.1 | 97.4 |
| 009 | 100 | 99.2 | 98.8 | 97.7 | 98.2 | 97.2 | 97.2 |
| 010 | 100 | 95.3 | 93.0 | 90.9 | 90.1 | 88.7 | 87.9 |
| 011 | 100 | 95.9 | 97.1 | 96.9 | 95.0 | 93.1 | 93.7 |
| 017 | 100 | 98.0 | 99.1 | 99.5 | 97.8 | 97.6 | 98.8 |
| 018 | 100 | 97.1 | 97.9 | 98.8 | 96.7 | 97.5 | 97.1 |

*study numbers 014-016, 019, and 020, as discussed in greater detail below, were not further examined.

Figure 6:
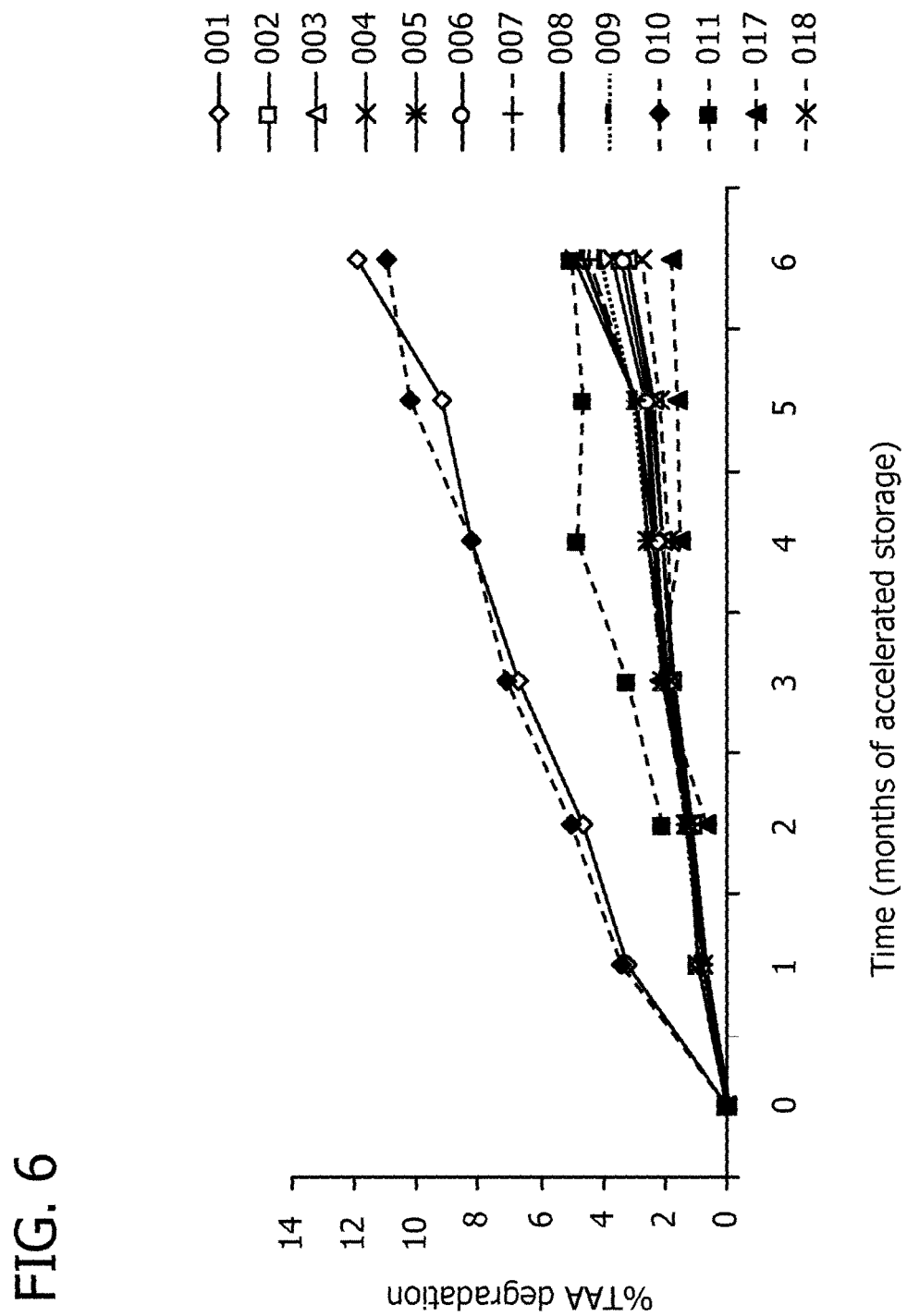
FIG. 6 is a graph depicting the stability of various TAA and lidocaine formulations as percent TAA degradation versus time as described in greater detail in Example 6.

Total percent of TAA degradants for the six months of accelerated storage were calculated by totaling the individual percent degradants for each of formulae I, II, and III, each individual percentage being determined according to the following formula, and are listed in Table 7 and depicted graphically in FIG. 6.

$$\% \ Imp = \frac{(Area \ Imp)}{(Area \ TAA + Area \ Imp \ I + Area \ Imp \ II + Area \ Imp \ III)} \times 100\%$$

TABLE 7

Total % TAA Degradants for 6 months of accelerated storage

| Lot# | 0-time | 1 m | 2 m | 3 m | 4 m | 5 m | 6 m |
|---|---|---|---|---|---|---|---|
| 001 | 0 | 3.2 | 4.63 | 6.74 | 8.2 | 9.16 | 11.92 |
| 002 | 0 | 0.96 | 1.18 | 1.97 | 2.29 | 2.59 | 3.43 |
| 003 | 0 | 0.91 | 1.1 | 1.8 | 2.11 | 2.39 | 3.21 |
| 004 | 0 | 0.98 | 1.22 | 2.05 | 2.36 | 2.67 | 3.66 |
| 005 | 0 | 0.75 | 1.2 | 1.88 | 2.51 | 2.89 | 4.92 |
| 006 | 0 | 0.76 | 1.21 | 1.78 | 2.2 | 2.58 | 3.33 |
| 007 | 0 | 0.79 | 1.33 | 2.04 | 2.59 | 2.95 | 4.43 |
| 008 | 0 | 0.77 | 1.25 | 1.88 | 2.38 | 2.96 | 4.59 |
| 009 | 0 | 0.82 | 1.33 | 2.01 | 2.53 | 3.05 | 4.03 |
| 010 | 0 | 3.4 | 5.03 | 7.06 | 8.26 | 10.22 | 10.98 |
| 011 | 0 | NA | 2.11 | 3.18 | 4.81 | 4.66 | 4.98 |
| 017 | 0 | NA | 0.69 | 2.18 | 1.5 | 1.61 | 1.78 |
| 018 | 0 | NA | 1.3 | 1.81 | 1.86 | 2.14 | 2.77 |

The total percent TAA degradants, as listed in Table 7 above and Table 9 below, represents the percentage of the 0.1 wt. % TAA degraded. Thus, for example, 001 has 11.92% degradation of the 0.1 wt. % TAA, or 0.012 wt. % TAA degradants, and 002 has 3.43% degradation of the 0.1 wt. % TAA, or 0.003 wt % TAA degradants. The total percent of TAA degradants listed in the table is the sum of percent TAA degradants of formulae I, II, and III.

Figure 7:
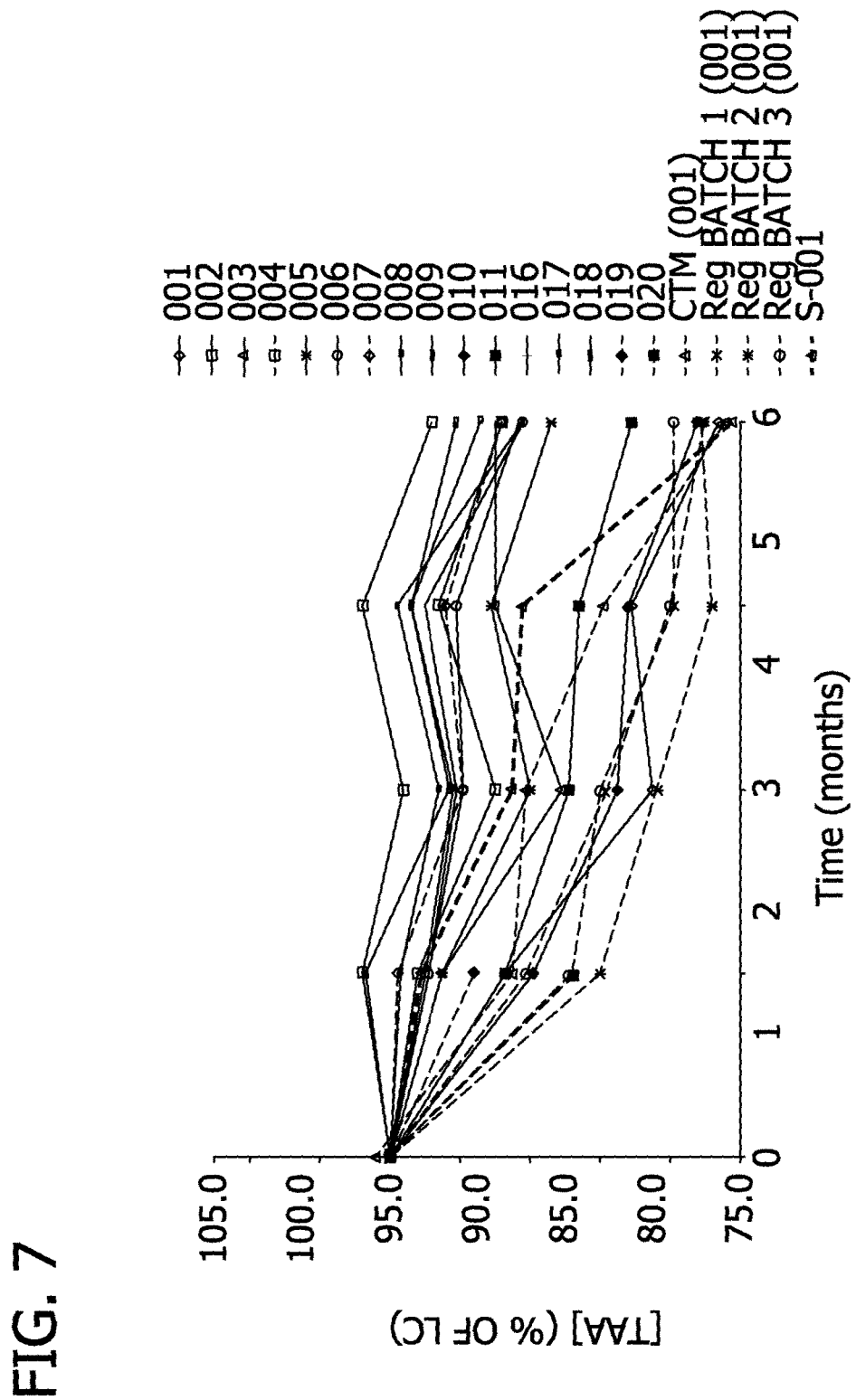
FIG. 7 is a graph depicting the stability of various TAA and lidocaine formulations at room temperature storage over a twelve month period as the concentration of TAA versus time as described in greater detail in Example 6.

Normalized TAA assay results for twelve months of room temperature stability storage were determined and are listed in Table 8 and depicted graphically in FIG. 7.

TABLE 8

Normalized TAA assay results for 12 months of room temperature stability storage

| Lot# | 0-time | 3 m | 6 m | 9 m | 12 m |
|---|---|---|---|---|---|
| 001 | 100 | 96.7 | 92.5 | 93.1 | 90.6 |
| 002 | 100 | 100.8 | 99.6 | 100.8 | 98.8 |
| 003 | 100 | 98.5 | 95.1 | 97.0 | 97.0 |
| 004 | 100 | 99.2 | 97.0 | 98.6 | 96.8 |
| 005 | 100 | 98.5 | 96.0 | 97.1 | 95.4 |
| 006 | 100 | 98.9 | 97.9 | 98.1 | 96.3 |
| 007 | 100 | 99.8 | 97.9 | 98.4 | 96.8 |
| 008 | 100 | 100.7 | 98.3 | 99.4 | 97.4 |
| 009 | 100 | 99.0 | 98.2 | 99.4 | 98.1 |
| 010 | 100 | 95.9 | 93.5 | 93.2 | 91.2 |
| 011 | 100 | 96.7 | 94.9 | 94.6 | 93.1 |
| 017 | 100 | 99.7 | 98.6 | 99.8 | 96.2 |
| 018 | 100 | 98.9 | 98.1 | 99.0 | 96.2 |

Figure 8:
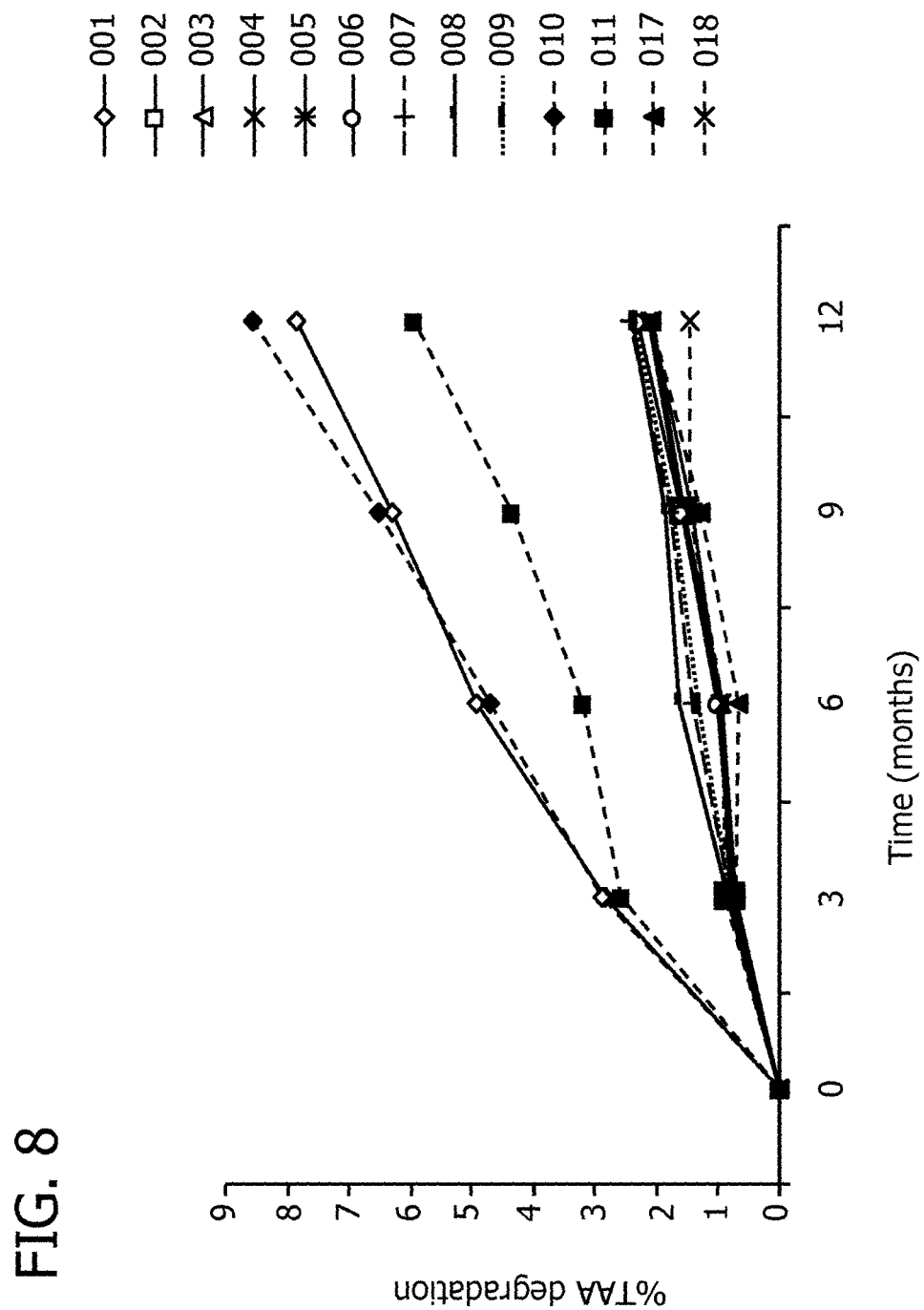
FIG. 8 graphically depicts the total percent of TAA degradants under accelerated storage conditions over a twelve month period as the percent of TAA degradants versus time as described in greater detail in Example 6.

Total percent of TAA degradants for the twelve months of room temperature storage were calculated by totaling the individual percent TAA degradants for each of formulae I, II, and III, each individual percentage being determined according to the following formula and are listed in Table 9 and depicted graphically in FIG. 8.

$$\% \ Imp = \frac{(Area \ Imp)}{(Area \ TAA + Area \ Imp \ I + Area \ Imp \ II + Area \ Imp \ III)} \times 100\%$$

TABLE 9

Total % TAA Degradants for 12 months of room temperature storage

| Lot# | 0-time | 3 m | 6 m | 9 m | 12 m |
|---|---|---|---|---|---|
| 001 | 0 | 2.84 | 4.92 | 6.3 | 7.83 |
| 002 | 0 | 0.72 | 0.94 | 1.53 | 2.1 |

TABLE 9-continued

Total % TAA Degradants for 12 months of room temperature storage

| Lot# | 0-time | 3 m | 6 m | 9 m | 12 m |
|------|--------|------|------|------|------|
| 003 | 0 | 0.81 | 0.99 | 1.44 | 2.09 |
| 004 | 0 | 0.73 | 0.97 | 1.6 | 2.29 |
| 005 | 0 | 0.69 | 0.96 | 1.59 | 2.12 |
| 006 | 0 | 0.74 | 1 | 1.61 | 2.29 |
| 007 | 0 | 0.8 | 1.44 | 1.79 | 2.43 |
| 008 | 0 | 0.84 | 1.65 | 1.88 | 2.38 |
| 009 | 0 | 0.79 | 1.32 | 1.74 | 2.35 |
| 010 | 0 | 2.89 | 4.68 | 6.5 | 8.57 |
| 011 | 0 | 2.58 | 3.21 | 4.35 | 5.93 |
| 017 | 0 | 0.73 | 0.68 | 1.28 | 2.07 |
| 018 | 0 | 0.88 | 0.93 | 1.45 | 1.47 |

Figure 9:
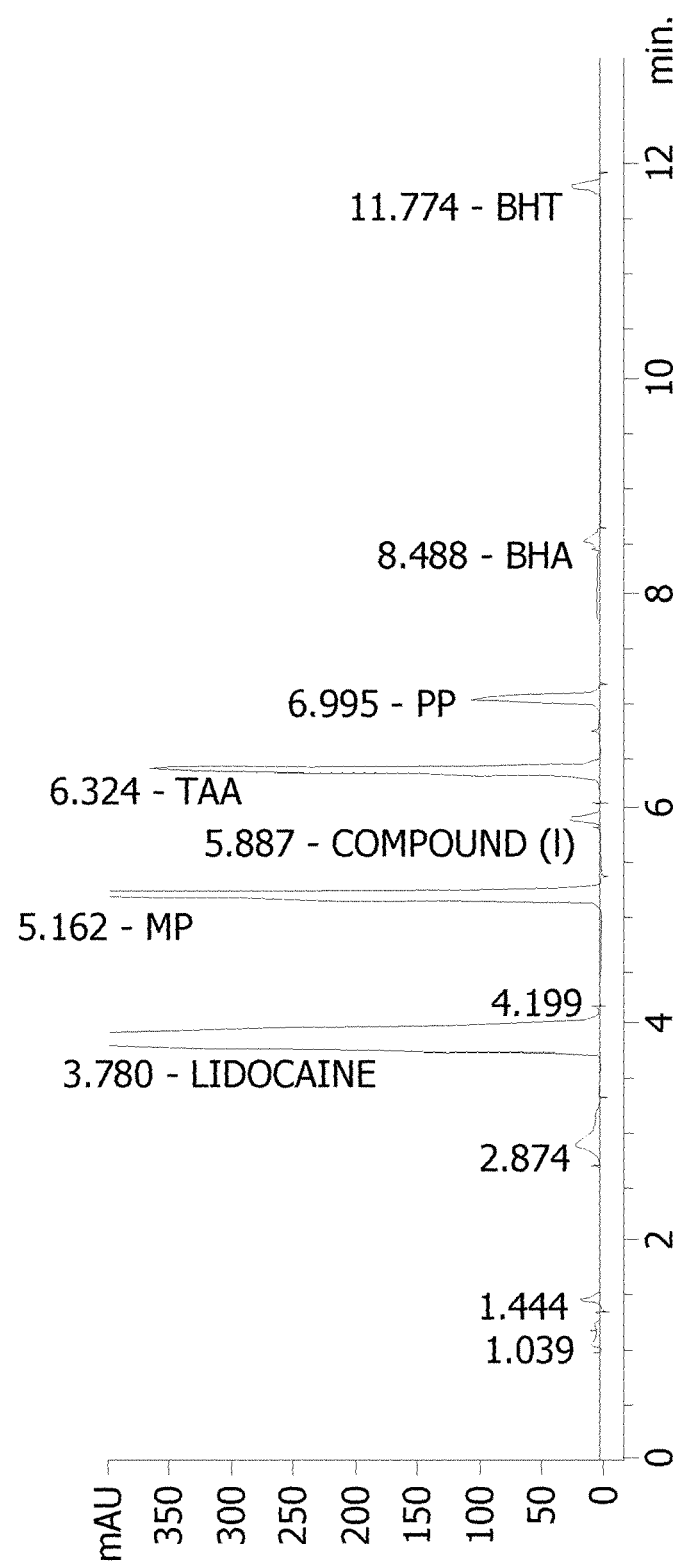
FIG. 9 is an HPLC chromatogram depicting the results of experiments as described in greater detail in Example 6.
Figure 10:
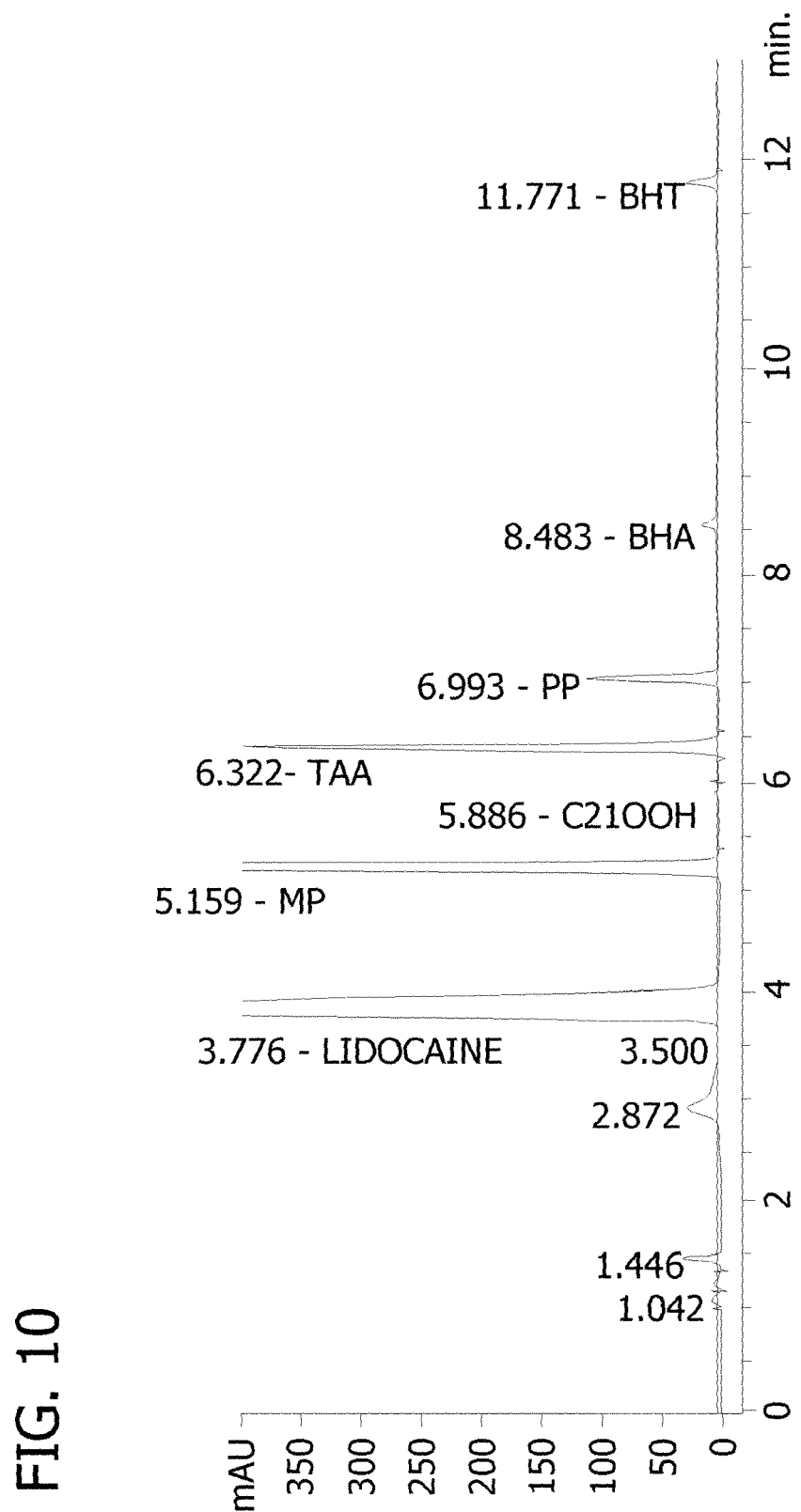
FIG. 10 is an HPLC chromatogram depicting the results of experiments as described in greater detail in Example 6.
Figure 11:
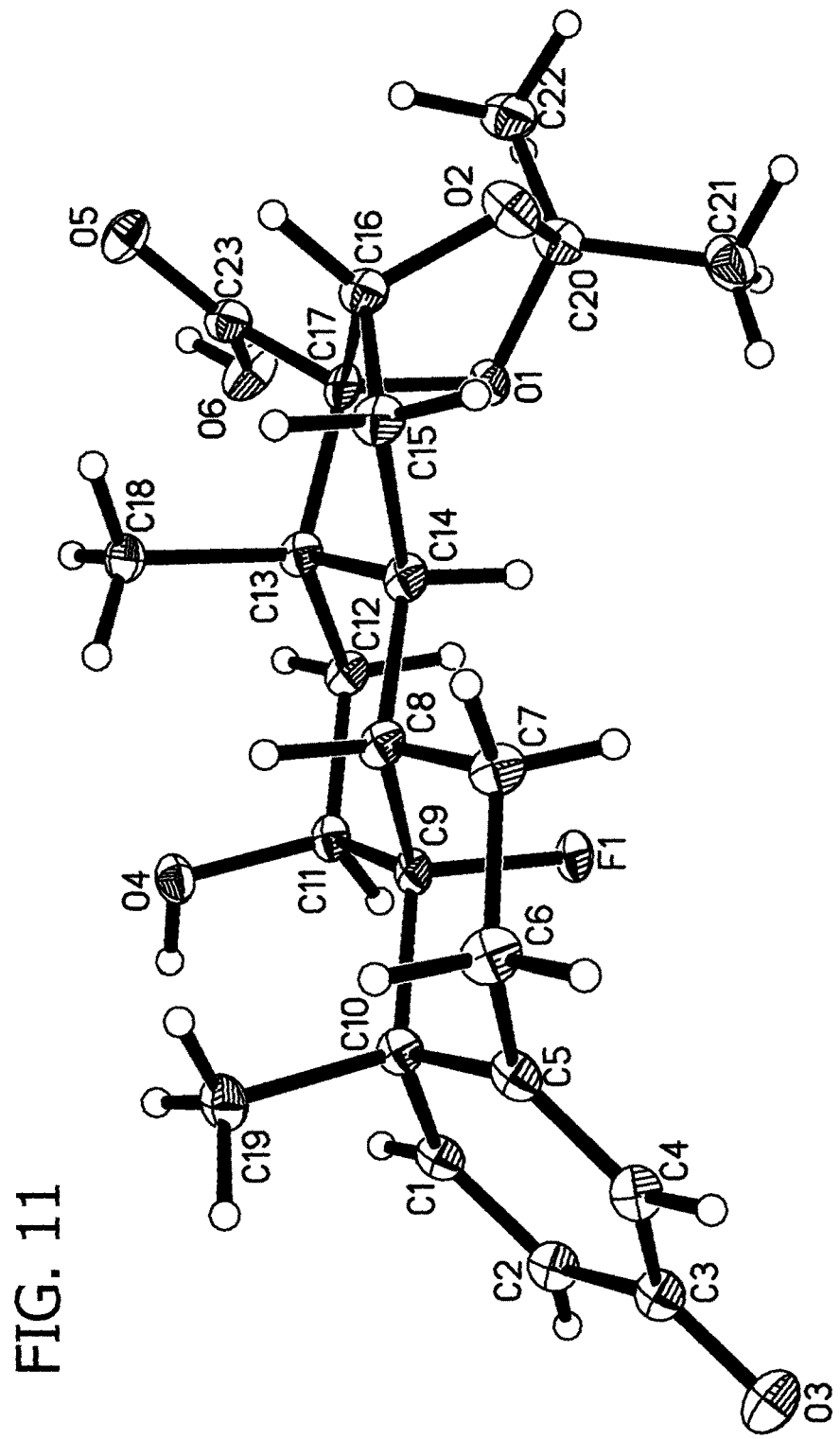
FIG. 11 is a graphical depiction of the crystal structure of Compound II as described in greater detail in Example 3.

Trials 001 and 003 were subjected to HPLC analysis. The results are represented in FIGS. 9 and 10, respectively, and demonstrate the reduced degradation of TAA (and likewise the decreased presence of compounds having the formulae I, II, or III) in formulation 003 versus formulation 001.

Example 7: Use of a Blanket of Inert Gas

This purpose of the following investigation was to determine the affects of producing a therapeutic compound under a blanket of inert gas. The S-001 batch listed in Table 10 was prepared using the Fryma MaxxD semi-solid manufacturing equipment. Studies S-002 through S-017 were performed at the Fryma process lab in Germany. S-017 was found to have inconsistent results indicating non-homogeneous product. As this material was from the same batch as studies S-015 & 016, it was concluded that the inconsistencies may have stemmed from a heating band malfunction which occurred during the packaging of S-017 (the last material in the batch to be packaged). Study S-017, which is a repeat of the data for S-013, was therefore excluded from further study.

TABLE 10

| Batch # | Study Code | Experiment Description |
|---------|------------|------------------------|
| 1 | S-001 | Formulation 001 of Example 6 |
| 2 | S-002 | Lab scale of S-001 |
| 3 | S-003 | Repeat of S-002 |
| 4 | S-004 | Lab scale of S-001 with process change to introduce the Gantrez with the PEG 3350 |
|   | S-005 | Repeat of S-004 except heat premix under vacuum to remove any water (premix sample held at 65 deg C. with 4 vacuum cycles ~ 30 min) |
|   | S-006 | Repeat of S-004 except heat premix under vacuum to remove any water (premix sample held at 85 deg C. for an additional 3 vacuum cycles ~ 25 min) |
|   | S-007 | Repeat of S-004 except heat premix under vacuum to remove any water (the final product formulated from the above premix S-006) |
| 5 | S-008 | Repeat of S-002 with extended heating (65 deg C.) hold under vacuum to remove water (3 vacuum cycles ~ 35 min) |
|   | S-009 | Repeat of S-002 with extended heating (85 deg C.) hold under vacuum to remove water (S-008 product held at 85 deg C for 3 vacuum cycles ~ 30 min) |
| 6 | S-010 | S-001 with dried Gantrez |
| 7 | S-011 | S-001 with manufacturing and packaging under nitrogen as well as secondary nitrogen filled foil pouch |
|   | S-012 | S-001 with manufacturing and packaging under nitrogen (S-011 without foil pouch) |

TABLE 10-continued

| Batch # | Study Code | Experiment Description |
|---------|------------|------------------------|
|   | S-013 | S-001 with manufacturing under nitrogen (S-011 without nitrogen blanket on tube filler/sealer) |
| 8 | S-014 | S-001 without Gantrez |
| 9 | S-015 | Repeat of S-011 |
|   | S-016 | Repeat of S-012 |
|   | S-017 | Repeat of S-013 |

Figure 12:
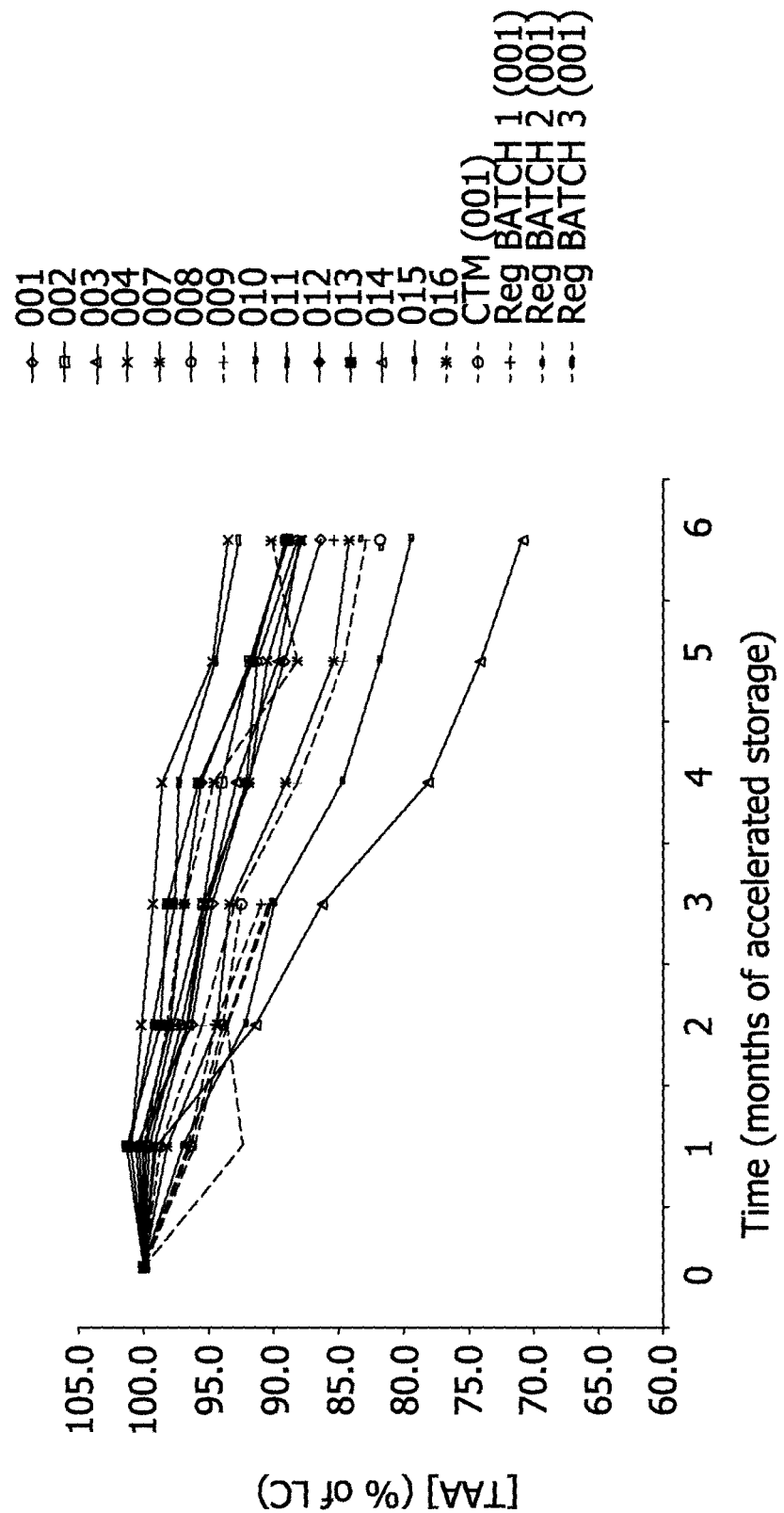
FIG. 12 is a graph depicting the accelerated stability of various TAA and lidocaine formulations as a percent recovery of TAA versus time as described in greater detail in Example 7.
Figure 13:
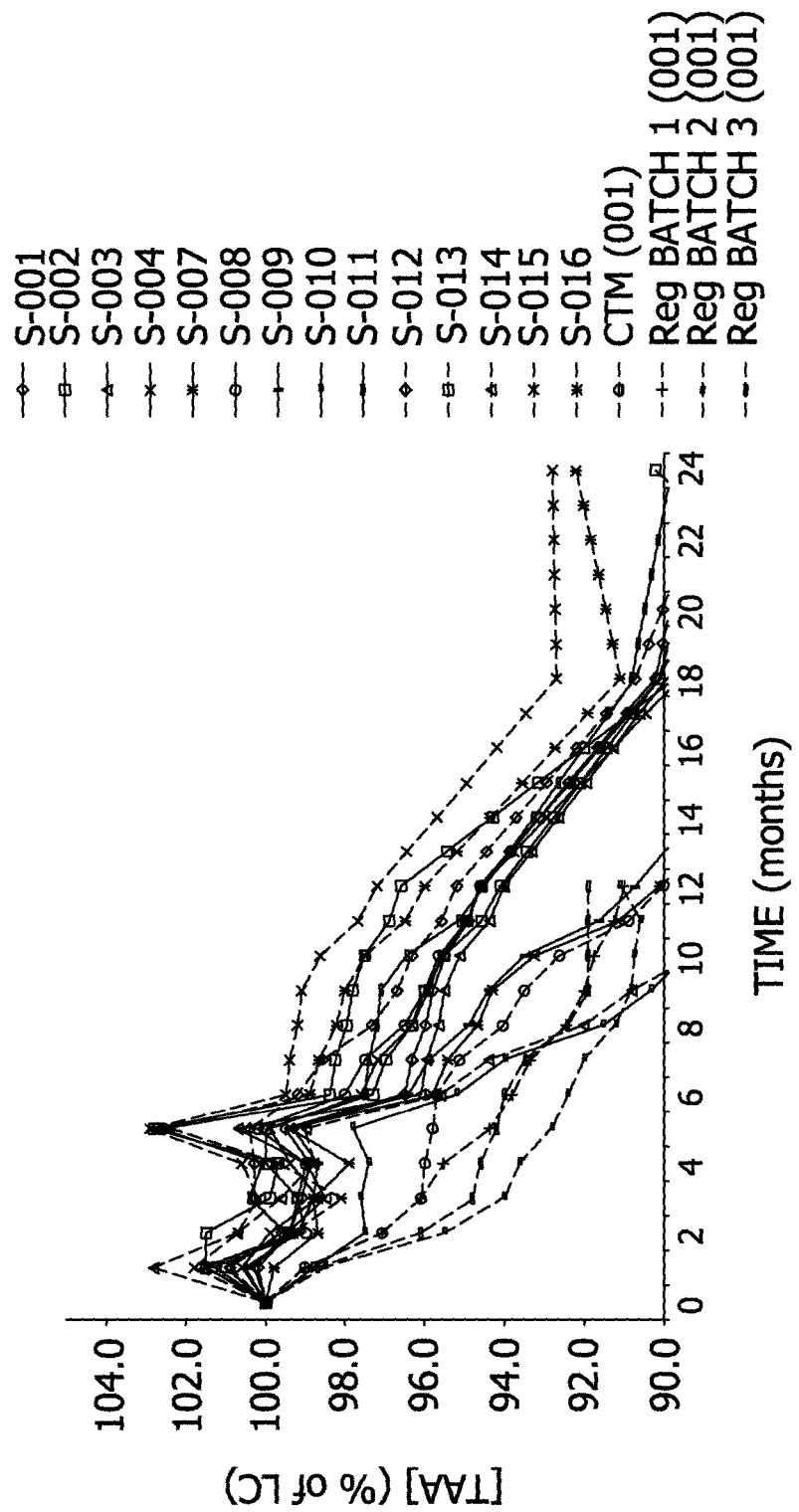
FIG. 13 is a graph depicting the stability of various TAA and lidocaine formulations as a percent recovery of TAA versus time as described in greater detail in Example 7.

The percent TAA recovery, obtained according to the accelerated stability storage methods discussed above for a six month period, is represented graphically in FIG. 12. The TAA recovery, obtained according to the standard stability storage methods discussed above for a 24 month period, is represented graphically in FIG. 13. For these studies, data regarding months 7, 8, 10, 11, 13-17, and 19-23 were calculated values based on observed values using data obtained for months 1-6, 9, 12, 18, and 24 (the standard test periods per the IHC). For the clinical trial material (CTM) batch and registration (Reg 1, Reg 2, and Reg 3) batches (the same formulation as Formulation 001 of example 6), data regarding months 7, 8, 10, and 11 were calculated values based on observed values using data obtained for months 1-6, 9, and 12.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained. As various changes could be made in the above methods without departing from the scope of the invention, it is intended that all matter contained in the above description and shown in any accompanying figures shall be interpreted as illustrative and not in a limiting sense.

What is claimed is:

1. A storage stable therapeutic composition for topical administration comprising:
    about 0.01 to 0.3% by weight triamcinolone acetonide;
    about 0.25 to about 6% by weight lidocaine hydrochloride;
    a base, the base comprising a water soluble salt of a copolymer of a lower alkyl vinyl ether and maleic acid or anhydride and a polyalkylene glycol;
    wherein the composition is free from butylated hydroxytoluene and free from butylated hydroxyanisole.

2. The composition of claim 1, further comprising a preservative.

3. The composition of claim 2, wherein the preservative is selected from methylparaben and/or propylparaben.

4. The composition of claim 1, wherein the polyalkylene glycol is polyethylene glycol (PEG).

5. The composition of claim 4, wherein the PEG is a mixture of low molecular weight PEG that is liquid at 30° C. and a high molecular weight PEG that is a waxy solid at 30° C.

6. The composition of claim 1, wherein the composition comprises at least about 90% triamcinolone acetonide based on the amount of said triamcinolone acetonide within the composition at the time of manufacture compared to the amount after 14 months storage at 25° C. and 60% relative humidity.

7. The composition of claim 1, wherein the composition comprises at least 90% of said lidocaine hydrochloride based on the amount of lidocaine hydrochloride within the composition at the time of manufacture after 6 months storage at 40° C. and 75% relative humidity.

8. The composition of claim 1 wherein the polyalkylene is chosen from at least one of polyethylene glycol 400, and polyethylene glycol 3350.

9. A method of treating an epidermal condition in a patient in need thereof, comprising:
providing a composition, the composition comprising about 0.01 to 0.3% by weight triamcinolone acetonide, about 0.25 to about 6% by weight lidocaine hydrochloride, a base that comprises a water soluble salt of a copolymer of a lower alkyl vinyl ether and maleic acid or anhydride and a polyalkylene glycol, wherein the composition is free from butylated hydroxytoluene and free from butylated hydroxyanisole; and
topically administering the composition to the area of an epidermal condition, wherein the epidermal condition is selected from the group consisting of eczema, bug bites, burns in mouth, aphthous ulcers, and external mouth sores.

10. A method of treating a condition of a patient's mouth, comprising:
providing a composition, the composition comprising about 0.01 to 0.3% by weight triamcinolone acetonide, about 0.25 to about 6% by weight lidocaine hydrochloride, a base that comprises a water soluble salt of a copolymer of a lower alkyl vinyl ether and maleic acid or anhydride and a polyalkylene glycol, wherein the composition is free from butylated hydroxytoluene and free from butylated hydroxyanisole; and
topically administering the composition to the mucosal area of a mouth condition, wherein the condition is selected from the group consisting of aphthous ulcers, burns in mouth, and external mouth sores.

* * * * *